US009910965B2

(12) United States Patent
Bufalini et al.

(10) Patent No.: US 9,910,965 B2
(45) Date of Patent: Mar. 6, 2018

(54) SYSTEMS, METHODS AND COMPUTER PROGRAM PRODUCT FOR MONITORING INTERACTIONS WITH A MEDICATION STORAGE DEVICE

(75) Inventors: Brian Bufalini, Aliquippa, PA (US); Fabian R. Reza, Pittsburgh, PA (US)

(73) Assignee: Aesynt Incorporated, Cranberry, PA (US)

( * ) Notice: Subject to any disclaimer, the term of this patent is extended or adjusted under 35 U.S.C. 154(b) by 905 days.

(21) Appl. No.: 13/235,178

(22) Filed: Sep. 16, 2011

(65) Prior Publication Data

US 2013/0070090 A1    Mar. 21, 2013

(51) Int. Cl.
*H04N 7/18* (2006.01)
*G06F 19/00* (2018.01)

(52) U.S. Cl.
CPC ........... *G06F 19/3462* (2013.01); *H04N 7/18* (2013.01)

(58) Field of Classification Search
USPC ....................................... 700/242, 241, 231
See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |
| 5,661,978 A | 9/1997 | Holmes et al. |
| D384,578 S | 10/1997 | Wangu et al. |
| 5,713,485 A | 2/1998 | Liff et al. |
| 5,716,114 A | 2/1998 | Holmes et al. |
| 5,745,366 A | 4/1998 | Higham et al. |
| 5,761,877 A | 6/1998 | Quandt |

(Continued)

OTHER PUBLICATIONS

The MPEG-4 Streaming Player Using Adaptive Decoding Time Stamp Synchronization D. Lee, N. Kim and S. Kim;' Computer Multimedia Lab., Dept. of Computer Science, Kyungpook National Univ., Korea Proceedings of the Ninth International Conference on Parallel and Distributed Systems (ICPADS'02) © 2002 IEEE.*

*Primary Examiner* — Andy Rao
*Assistant Examiner* — Samuel D Fereja
(74) *Attorney, Agent, or Firm* — Alston & Bird LLP

(57) ABSTRACT

Methods, apparatuses and computer program products are provided for monitoring the stocking and dispensing of medications from an automated medication storage device. In this regard, a method may cooperate with the automated medication storage device to facilitate surveillance of internal components and users of the medication storage device. For example, a user and/or the user's interactions can be imaged by one or more cameras while the user is interacting with the automated medication storage device.

18 Claims, 10 Drawing Sheets

(56) References Cited

U.S. PATENT DOCUMENTS

| | | |
|---|---|---|
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,151,536 A | 11/2000 | Arnold et al. |
| 6,170,230 B1 | 1/2001 | Chudy et al. |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,271,022 B1 * | 8/2001 | Bochner ............... G01N 35/028 356/388 |
| 6,283,322 B1 | 9/2001 | Liff et al. |
| 6,289,656 B1 | 9/2001 | Wangu et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 | 4/2002 | Chudy et al. |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,539,281 B2 * | 3/2003 | Wan et al. .................... 700/236 |
| 6,564,121 B1 | 5/2003 | Wallace et al. |
| 6,581,798 B2 | 6/2003 | Liff et al. |
| 6,609,047 B1 | 8/2003 | Lipps |
| 6,611,733 B1 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,571,024 B2 | 8/2009 | Duncan et al. |
| 7,588,167 B2 | 9/2009 | Hunter et al. |
| 7,693,603 B2 | 4/2010 | Higham |
| 8,073,238 B2 * | 12/2011 | Nakanishi et al. ........... 382/141 |
| 8,145,353 B1 * | 3/2012 | Cotner .......................... 700/241 |
| 2004/0099683 A1 * | 5/2004 | Shows et al. ................. 221/263 |
| 2005/0062238 A1 * | 3/2005 | Broadfield et al. ............... 280/1 |
| 2005/0288571 A1 * | 12/2005 | Perkins et al. ................ 600/407 |
| 2006/0085094 A1 * | 4/2006 | Duncan et al. ................ 700/236 |
| 2007/0158357 A1 * | 7/2007 | Yuyama et al. .................. 221/2 |
| 2007/0294105 A1 * | 12/2007 | Pierce ................................ 705/2 |
| 2008/0119958 A1 * | 5/2008 | Bear ..................... A61J 7/0481 700/244 |
| 2008/0294018 A1 * | 11/2008 | Kurtz et al. ................... 600/301 |
| 2009/0091453 A1 * | 4/2009 | Ishida et al. ................ 340/572.1 |
| 2009/0138122 A1 * | 5/2009 | Wagner ........................ 700/226 |
| 2009/0161941 A1 * | 6/2009 | Nakanishi et al. ........... 382/141 |
| 2009/0187274 A1 * | 7/2009 | Higham ....................... 700/237 |
| 2009/0276317 A1 * | 11/2009 | Dixon et al. ................. 705/14.61 |
| 2010/0045423 A1 * | 2/2010 | Glickman et al. ............. 340/5.1 |
| 2010/0121482 A1 * | 5/2010 | Jackson et al. ............... 700/217 |
| 2011/0030034 A1 * | 2/2011 | Ross ................................ 726/4 |
| 2011/0196785 A1 * | 8/2011 | Meek et al. .................... 705/39 |
| 2011/0275432 A1 * | 11/2011 | Lutnick et al. ................. 463/25 |
| 2013/0076898 A1 * | 3/2013 | Philippe et al. ............... 348/143 |
| 2013/0173287 A1 * | 7/2013 | Cashman et al. ................ 705/2 |

\* cited by examiner

SYSTEMS, METHODS AND COMPUTER PROGRAM PRODUCT FOR MONITORING INTERACTIONS WITH A MEDICATION STORAGE DEVICE

TECHNOLOGICAL FIELD

Embodiments of the present invention relate generally to image capturing devices and associated methods and, more particularly, to image capturing devices and associated methods that aid in monitoring the removal from or placement of medication(s) within the medication storage device.

BACKGROUND

Medication dispensing cabinets have been developed to store and controllably dispense a variety of medications. A medication dispensing cabinet may include a cabinet body with one or more drawers that are slideably disposed within the cabinet body. The drawers store the various medications. While some of the drawers may be unlatched and freely openable, other drawers may be locked in order to more closely control access to the medications stored in the locked drawers.

Some medication dispensing cabinets are automated and, as such, include or are otherwise associated with a computer that controls access to the compartments that store medications within the cabinet. The computer may allow access to only authorized users, such as pharmacists and pharmacy technicians who stock the cabinet and medical providers who dispense medications from the cabinet to patients.

As a result, when medication goes missing, there are usually at least two people who have entered the compartment in which the missing medication should have been stored. The first person may be a pharmacist or other user who was supposed to have stocked the medication into the compartment or a nurse who first accesses the compartment to dispense medication. The second person may be another nurse who subsequently accesses the compartment and discovers (and reports) medication as missing. In some instances, there may have been even more people interacting with the cabinet before the medicine is reported as missing.

Upon discovering that medication is missing, an investigation is often required to determine the cause of the discrepancy. Unfortunately, it may often times be challenging to conclusively determine the cause of the discrepancy.

BRIEF SUMMARY

Methods, apparatuses and computer program products are provided according to embodiments of the present invention for monitoring user interactions with a medication storage device and/or components thereof. In some embodiments, a storage device for dispensing medications is provided. The storage device can comprise at least one drawer configured to store a plurality of medications and at least one medication observation camera integrated into the storage device. The medication observation camera can be configured to capture one or more images of a user's interactions with at least one of the medications stored in the drawer, which are sometimes referred to herein as "medication images."

In some embodiments, the medication observation camera can be configured to begin capturing the images of the user's interactions with medications in response to a determination by a processor that the drawer is open and/or is otherwise accessible (e.g., unlocked, etc.). The medication observation camera can be integrated into the drawer of the storage device.

In some embodiments, the storage device can further comprise at least one user observation camera, in addition to or instead of the medication observation camera, that is configured to capture one or more images of the user, which are sometimes referred to herein as user images. In this regard, the medication observation camera can have an "internal field of view" whereas the user observation camera can have an "external field of view," where the terms "internal" and "external" are relative to the storage device. In some embodiments, the user observation camera can be configured to capture the user images while the medication observation camera captures the medication images of a field of view directed at internal components of the storage device.

The storage device can further comprise a processor that is configured to: receive a command from a remote machine; and in response to receiving the command, cause the transmission of a video feed to the remote machine, the video feed including image data that represents the images of interactions inside the storage device. The processor can also or instead be configured to: receive medication image data representing the medication images captured by the observation camera; and cause the transmission of the medication image data to the remote machine. At least one user observation camera can also be configured to capture one or more user images of the user, and the processor can be further configured to: cause the transmission of user image data to the remote machine, the user image data representing the user images, wherein the user image data and the medication image data of internal interactions both include metadata (such as time stamps) that enable the user image data and the medication image data of internal interactions to be synchronized in time.

Moreover, in some embodiments, the storage device can comprise a display device configured to present a graphical user interface display, and the processor can be further configured to: generate display data that causes the presentation of the graphical user interface display; and cause the transmission of the display data, wherein the display data includes metadata that enables the display data, the user image data and the medication image data of internal interactions to be synchronized in time.

In some embodiments, a medication storage device is provided that comprises a drawer, the drawer comprising: a recess configured to receive an image capturing device; and an image capturing device configured to be stowed in the recess. The image capturing device can include a beveled edge that is configured to drive the image capturing device into the recess in response to the drawer being placed in a closed position within the medication storage device. The image capturing device can include a spring that is configured to drive the image capturing device from the recess into a viewing position in response to the drawer being placed in an open position relative to the medication storage device. The viewing position can enable the image capturing device's field of view to include a user's interactions with one or more compartments (e.g., pockets) in the drawer used to store medication. The image capturing device can also be configured to automatically begin capturing images in response to being placed into the viewing position.

In instances in which embodiments herein are used to capture and combine video and/or other images of the user and his/her interactions with the medication storage compartment(s) as well as the on-screen events (such as the user's interactions with graphical user interface displays), synchronize the events and images together using time stamps and/or other metadata, and give administrators the ability to see the events and images played back at a moment's notice and on demand by the administrator, many of the common techniques used to divert narcotics will be caught much more quickly if not deterred altogether. Furthermore, embodiments discussed herein can include optional microphones to monitor users' conversations at the storage device and/or additional internal or external cameras for monitoring the entire medication room or to provide more fields of view and/or different viewing angles.

The above summary is provided merely for purposes of summarizing some example embodiments of the invention so as to provide a basic understanding of some aspects of the invention. Accordingly, it will be appreciated that the described embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIGS. 5-6D illustrate various views of a drawer and a drawer monitoring device integrated in the drawer in accordance with some example embodiments discussed herein;

DETAILED DESCRIPTION

Figure 1:
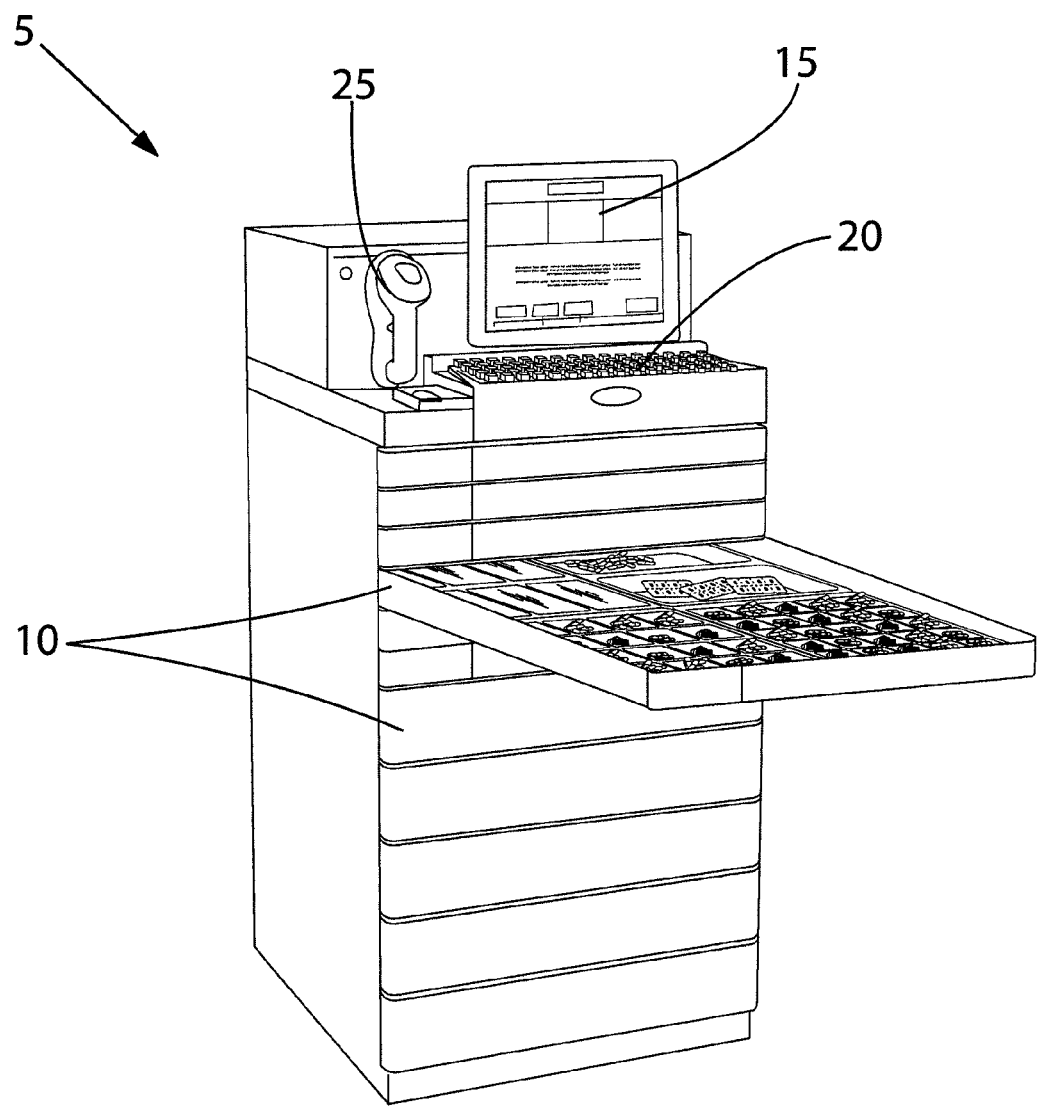
FIG. 1 illustrates an automated storage device in accordance with some example embodiments discussed herein.

Embodiments of the present inventions now will be described more fully hereinafter with reference to the accompanying drawings, in which some, but not all embodiments of the inventions are shown. Indeed, embodiments of these inventions may be embodied in many different forms and should not be construed as limited to the embodiments set forth herein; rather, these embodiments are provided so that this disclosure will satisfy applicable legal requirements. Like reference numerals refer to like elements throughout.

The storage devices, systems, and methods of embodiments of the present invention may be used by healthcare facilities, such as hospitals, physicians' offices, healthcare clinics, and any other facility that manages and/or dispenses drugs and/or other materials for patient use. The storage devices, systems, and methods described herein are configured to assist in providing, among other things, (1) a reduction in the likelihood of narcotic diversion, (2) assistance in investigating narcotic diversion, (3) verification of the user during a given narcotic transaction, (4) the ability to survail certain users that administrators want to monitor for potential diversion, and/or (5) an effective, practical and cost effective alternative or addition to a second human being that acts as a witness during a narcotic transaction. While some embodiments are discussed herein in reference to narcotics diversion, embodiments of the invention are not limited to monitoring for and/or reducing narcotic diversion. Further, although pharmacists and nurses are often tasked with stocking and accessing medication stored in an automated storage device, and examples with a pharmacist and/or nurse are sometimes used in the description that follows, it is understood that the described embodiments apply to any user who is interfacing with the automated storage device, including pharmacists, pharmacy technicians, nurses, physicians, administrators, laboratory personnel, respiratory therapists, and others. Furthermore, although the examples of a user interfacing with an automated storage device for the purposes of restocking and dispensing medications are predominantly described below, one skilled in the art in light of this disclosure would recognize that the embodiments are also applicable to users interfacing with the automated storage device for the purpose of taking inventory, and performing other tasks that may require access to the medication storage compartments in the automated storage device. In addition, the phrase "storage device" is intended to include any type of automated storage device, including an automated dispensing cabinet (ADC), unit-based cabinet (UBC), automated dispensing device (ADD), automated distribution cabinet, medication dispensing cabinet, and automated dispensing machine (ADM), among others. And the use of "dispensing" herein refers to any type of removal of any object from a storage device for any reason, and is not limited to, for example, the dispensing of medication by a nurse for administration to a patient.

Turning now to FIG. 1, a storage device 5 is shown. For example, some embodiments of the storage device 5 can be similar to and/or include components that are currently included in the cabinets sold and marketed as McKesson's AcuDose-Rx® and/or Anesthesia-Rx™ cabinets. The storage device 5 may be configured to store a number of different types and quantities of medications. In this regard, the storage device 5 may include (e.g., define) a plurality of drawers 10. Different types of storage devices 5 may include different sizes and styles of drawers 10, depending on, for example, the types of medications to be stored in the drawers, the quantities required (which may be dictated by the size or type of the facility or other area serviced by the automated storage device), and user preferences. In addition, access to the drawers 10 may be restricted to certain authorized users and may further be accessible only when medication stored in the particular drawer is to be dispensed, as described in greater detail below. Accordingly, each drawer 10 may be in a locked state until an authorized user interfaces with the storage device 5 to select for dispensing a particular medication stored within a particular drawer, at which point the storage device may unlock and/or open the drawer containing the selected medication to allow the user's access. Additionally, one or more drawers may include and/or otherwise be monitored by one or more cameras, as described in greater detail below.

The drawers 10 may hold more than just medications, in some cases. For example, certain medical accessories or supplies may also be stored in the automated storage device 5, such as applicators, syringes, keys, prescription pads, cameras, etc., which may also be dispensed, stocked, and/or otherwise handled by the user during an interaction with the storage device. Accordingly, although the examples provided below refer to the dispensing and/or stocking of medications, the dispensing, stocking, transport and/or other type of handling of any item stored in the storage device 5, such as medical accessories, is contemplated herein.

In some embodiments, the storage device 5 further includes a display device 15. The display device 15 may be a monitor, as depicted in FIG. 1, and may be configured to present various items of medication stocking information and/or dispensing information related to a selected patient for the user to view, as described below. For example, the storage device 5 may generate graphical user interface data that allows the user to be able to view medication dispensing information regarding the patients assigned to a particular nurse's shift or other patients to whose records the nurse has access, as well as medication dispensing information relating to the medications stored in the storage device 5 and/or other storage devices in communication with the storage device 5. The storage device 5 may also be connected to one or more other machines via a network, as described below, and may generate data that can be used by the remote machines to present a graphical user interface display, such as the example discussed in connection with FIG. 11.

The display device 15 may enable the user to be able to view a list of patients under the user's care; view patient details (e.g., patient's name, date of birth, medical condition, allergies, date of admittance, date of expected discharge, etc.); view a list of prescribed medications for a particular patient; view medication details (such as potential interactions, medication properties, and dosage information); and/or view order details (such as the name of a medication, required dosage, quantity to be dispensed, location of the medication in the storage device (drawer and pocket), etc.). Some or all of the user's interactions at the storage device 5, including those with the graphical user interfaces presented by the display device 15, may be monitored at a remote machine and/or recorded for future monitoring at the storage device 5 and/or at a remote machine.

Similarly, the display device 15 may also be configured to function as one or more input devices. For example, the display device 15 may have one or more cameras 35 and 40 integrated therein, as described below.

As another example, the display device 15 may include one or more touch-sensitive components and associated hardware, software and/or firmware. Additionally or alternatively, the storage device 5 may have one or more dedicated user input devices, such as the user input device 20 and/or user input device 25 shown in FIG. 1. The various user input devices that can be used with or included in the storage device 5, e.g., the display device 15, the user input device 20 and user input device 25, are sometimes referred to herein as "user input devices." The components that facilitate the generation of electrical signals associated with a user's interaction with the user input device are sometimes referred to herein as "user input components." For example, the display device 15 may function as both a user input and output device. Its touch-sensitive components may be considered user input components and its display components may be considered user output components. Other examples of user output components include lights, audio speakers, haptic feedback components, and/or any other device that may generate stimuli detectable by a user.

User input devices may be configured to receive input from the user regarding at least one dispensing transaction, and other input devices, such as one or more cameras, can be activated in response to determining a dispensing transaction is occurring and/or about to occur. In this regard, the term "dispensing transaction" is used herein to describe the interfacing between the user and the storage device to dispense one or more medications to be administered to a single patient. Thus, each dispensing transaction is associated with a particular selected patient. Furthermore, each user may have multiple dispensing transactions with the storage device in a single interaction with the storage device. In this regard, the window between the time a user logs into the system (e.g., provides identification credentials indicating that the user is authorized to have access to the medications stored within the storage device) to the time the user logs out of the system (which may require, e.g., a log-out event by the same user or resulting from an expiration of a predetermined period of time, or a log-in event by a different user for access to the storage device) may define the interaction, whereas the time it takes for the user to dispense medications relating to a particular patient may define the dispensing transaction. In some embodiments, one or more cameras and/or other input devices (e.g., microphones) may be used to monitor one or more user interactions with the storage device. Thus, a user may have multiple dispensing transactions for one or more patients in a single user interaction with the storage device.

With continued reference to FIG. 1, one or more user input devices may be configured to receive user input regarding a particular dispensing transaction. For example, a user input device may receive input in the form of identification credentials authorizing the user to access the storage device 5 and/or a particular drawer 10 of the storage device 5; a selection of a patient for whom medication is to be dispensed; a request for information regarding a particular medication stored in one of the drawers or a particular patient to whose records the user has access; a selection of a particular medication to be viewed or dispensed; and so on. As another example, the user input device(s) may be configured to receive user input regarding an inventory of a particular drawer 10 or multiple drawers, such as a count of the medications remaining in a particular drawer or pocket of the drawer after a medication has been dispensed. Furthermore, in some cases, the storage device 5 may be configured to communicate with other storage devices in other parts of the healthcare facility, such that the user may be able to enter input requesting information regarding the contents of the other storage devices.

Different types of storage devices 5 may include different sizes and styles of drawers 10, depending on the types of medications to be stored in the drawers, the quantities required (which may be dictated by the size of the facility), and user preferences. Access to the drawers 10 may be restricted to certain authorized users and may further be accessible only when medication stored in the particular drawer is to be dispensed, as described in greater detail below. Additionally or alternatively, each pocket may also be locked with a lid that the storage device 5 is configured to unlock only when medication stored in the particular pocket is to be dispensed or restocked. For example, each drawer 10 and/or pocket may be in a locked state until an authorized user interfaces with the storage device 5 to dispense or restock a particular medication stored within a particular drawer and/or pocket, at which point the storage device may unlock and/or open the drawer and/or pocket associated with the medication to allow the user's access. In some cases, the storage device 5 may unlock all of its drawers 10, all its pockets or all its pockets within a given drawer upon determining a particular user's authorization level to the storage device, regardless of the specific location(s) of the particular medication requested.

Figure 2:
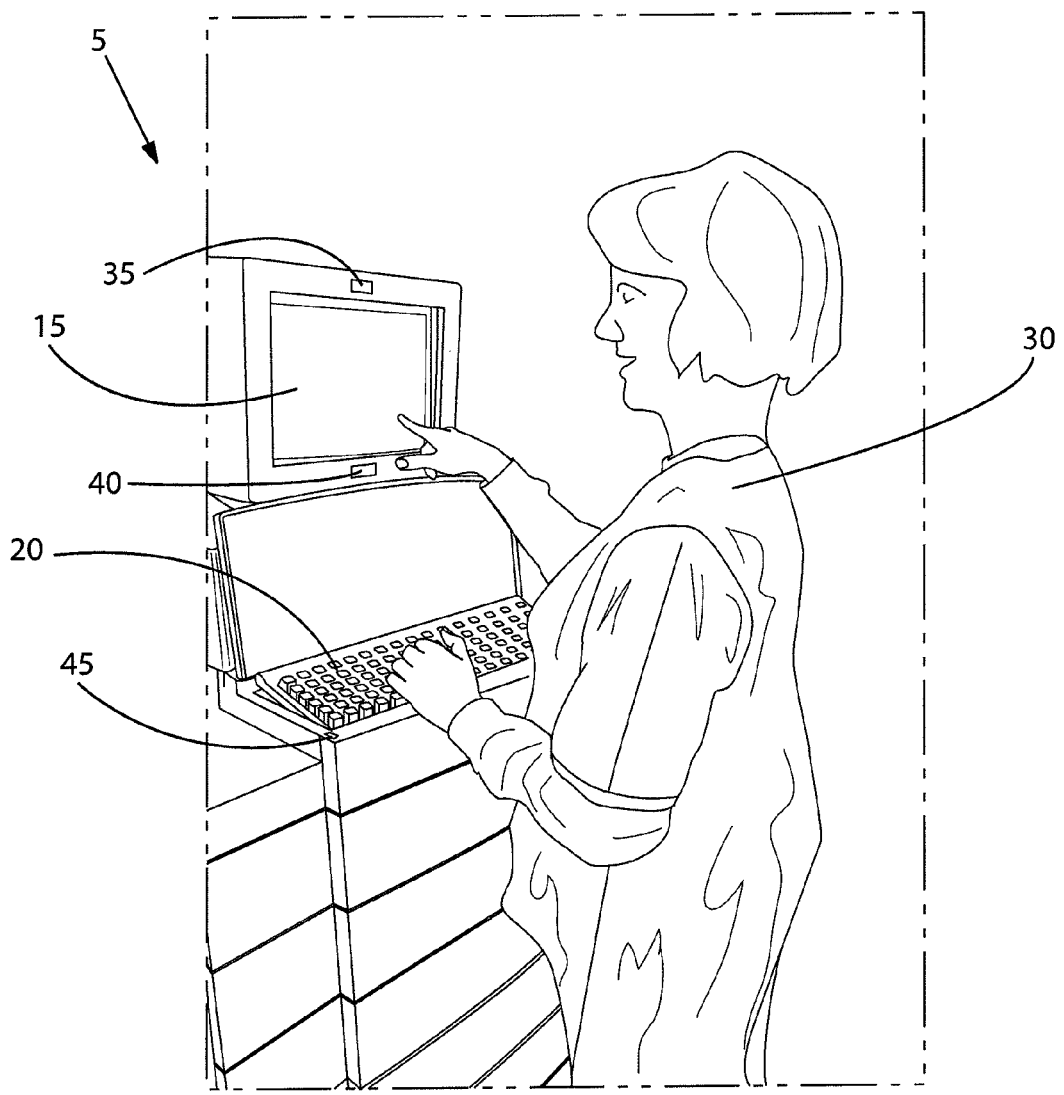
FIGS. 2-4 illustrate a user interacting with automated storage device in accordance with some example embodiments discussed herein.

As noted above, more than one user input device may be included in and/or configured to interface with the storage device 5. For example, as shown in FIGS. 1 and 2, the storage device 5 includes the display device 15, the user input device 20 in the form of a keyboard and the additional user input device 25 in the form of a barcode reader. The barcode reader may be configured to scan barcodes off medication packaging, and/or the barcode reader may be configured to read a user's identification credentials (e.g., badge, bracelet, key, etc.) to ascertain whether the user has access to a particular storage device and/or access to a particular medication, as well as to track and trend access to the storage device, such as for taking inventory and generating reports regarding users. Other examples of user input devices may include a mouse, microphone, biometric reader, and/or a camera, among others, some of which are discussed below.

The storage device 5 may also include one or more other components and/or may provide one or more other functions not specifically discussed herein. For example, the storage device 5 may include a container dispensing device mounted to or otherwise supported by the storage device. The container dispensing device may be configured to store and dispense containers, and each container may be configured to receive one or more dispensed medications for administering to a single selected patient. Thus, each container may be configured to allow the secure transport of the dispensed medications received therein between the storage device 5 and the selected patient's bedside.

As shown in FIG. 2, the location of the display device 15 and the various other user input devices of the storage device 5 allows the user 30, such as the nurse or pharmacist, to have comfortable access to the display device 15 and the user input devices discussed above when standing in front of the storage device 5. In this way, the user 30 may be able to view and manipulate various types of medication information upon first approaching the storage device 5, in the standing position (e.g., before accessing any of the drawers 10 to dispense medication), and the storage device 5 may include one or more cameras or other types of imaging devices that can view the user 30.

For example, the storage device 5 is shown in FIG. 2 as including two external image capturing devices, namely cameras 35 and 40, integrated into the display device 15 as well as an internal image capturing device, namely camera 45, integrated in the storage device 5 above its drawers. It is noted that, as used herein, the terms "external" and "internal" are meant to refer to the primary field of view of an image capturing device (e.g., primarily focused on internal components of the storage device 5 or primarily focused on items external to the storage device 5), as opposed to the physical location of the image capturing device (e.g., an external image capturing device may be located inside or otherwise integrated into a component of the storage device 5, while the internal image capturing device may be located external to any component of the storage device 5 to provide a vantage point of internal components).

The external image capturing devices can be configured to primarily capture the user 30 (or users) at the storage device 5. This way, if the user 30 is working in the bottom drawer of the storage device 5, the system can be configured to verify that the user 30 did not step out of the line-of-sight of the cameras 35 and/or 40, and/or that the user 30 is still indeed the same person, among other things. The external cameras can also be configured to serve potentially as a "witness" for narcotic transactions that may currently require two people be involved (per, e.g., the rules of the facility that is responsible for the narcotics).

Internal image capturing devices, such as camera 45, can be configured to log and/or otherwise capture images of the activity for any pocket and/or other compartment of the storage device 5. For example, when integrated with McKesson's AcuDose-Rx® and/or Anesthesia-Rx™ cabinet product lines, any cabinet event involving, e.g., a narcotic transaction can be a trigger event that causes activation of the external cameras 35 and 40 and the internal camera 45 for the drawer(s) being targeted by the user 30 and/or the storage device 5. Both internal and external image capturing device feeds can be synchronized by, e.g., the circuitry (e.g., processor) of the storage device 5, and/or a time stamp of the transaction (which may be in the form of metadata associated with the image data) can be generated and/or stored. When the transaction is complete, the storage device 5 can be configured to cease image capturing functionality of one or more of the image capturing devices. In this regard, administrators and/or other types of users can review, e.g., narcotic transactions that may be scrutinized for diversion or to clear up a discrepancy that may have occurred at the storage device 5.

Cameras 35, 40, and/or 45, like the other image capturing devices discussed herein, may be any type of image capturing device, including those that are sensitive to visual light, infrared light, ultraviolet light, and/or any other bands of light. Similarly, the image capturing devices discussed herein or otherwise integrated into a storage device can be configured to capture video and/or still images.

Cameras 35, 40, 45 and/or any other image capturing devices included in the storage device 5 may aid in enabling the storage device 5 and/or a system to which the storage device 5 belongs to facilitate various monitoring and/or surveillance functionality. For example, when the user 30 initially interfaces with the display device 15 and/or the user input device(s) 20, 25 to log-in, one or more sets of the cameras 35, 40 and/or 45 may be activated. Examples of methods for using the camera(s) are discussed in connection with FIGS. 9-10 and generally include, for example, improved processes for identifying a user, authorizing a user, recording and/or monitoring (e.g., witnessing) transactions with the storage device 5 (including the stocking and/or dispensing of medications), reducing the likelihood of narcotic diversion, assisting in investigations of unaccounted for medications (e.g., missing, lost or stolen medications), among other things.

Figure 3:
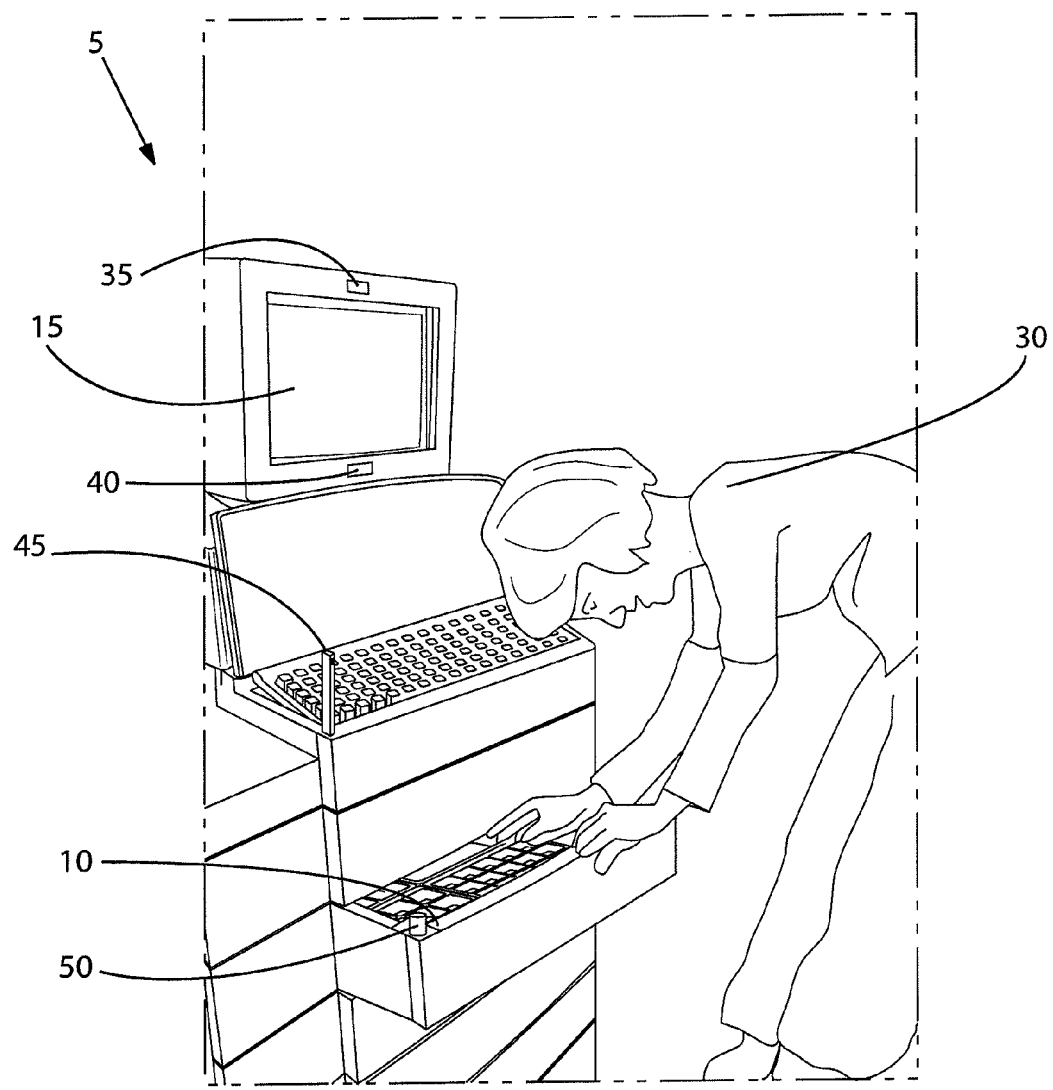

In some cases, after the user logs-into the storage device 5, the display device 15 and/or various other output devices may be used to direct the user 30 as to which drawer and/or pocket should be accessed to dispense the selected medication. The storage device 5 may also be configured to unlock the appropriate drawer(s) and/or other types of storage compartments. At any point and/or in response to one or more predetermined trigger events occurring (e.g., the user successfully logging into the storage device 5, the storage device 5 unlocking a drawer, the storage device 5 determining the user has opened a drawer, etc.), the storage device 5 (e.g., its processor and/or other control circuitry included therein) can be configured to activate one or more additional cameras that may have initially remained inactive. For example, cameras 35 and 40 may be used to identify a user during the log-in process, but once the user is logged in, camera 45 may be activated and/or raised, as shown in FIG. 3, to provide a vantage point for surveillance of the user's interactions with the drawer 10 and/or any other compartment(s) of the storage device 5. Additionally or alternatively, one or more image capturing devices may be included elsewhere in the storage device, such as drawer monitoring device 50 shown in FIGS. 3 and 5-6D as being included in the drawer 10. The drawer monitoring device 50 may be activated, for example, in response to a determination being made that its associated drawer (drawer 10 in the shown example) has been or is being opened, unlocked and/or has become otherwise accessible, in response to detecting ambient light (with, e.g., a separate sensor and/or the drawer monitoring device 50), in response a determination that the drawer monitoring device 50 has been deployed (e.g., as discussed in connection with FIGS. 6A-6D), and/or in response to any other trigger event(s) (some additional examples of which are discussed in connection with FIGS. 9 and 10).

Figure 4:
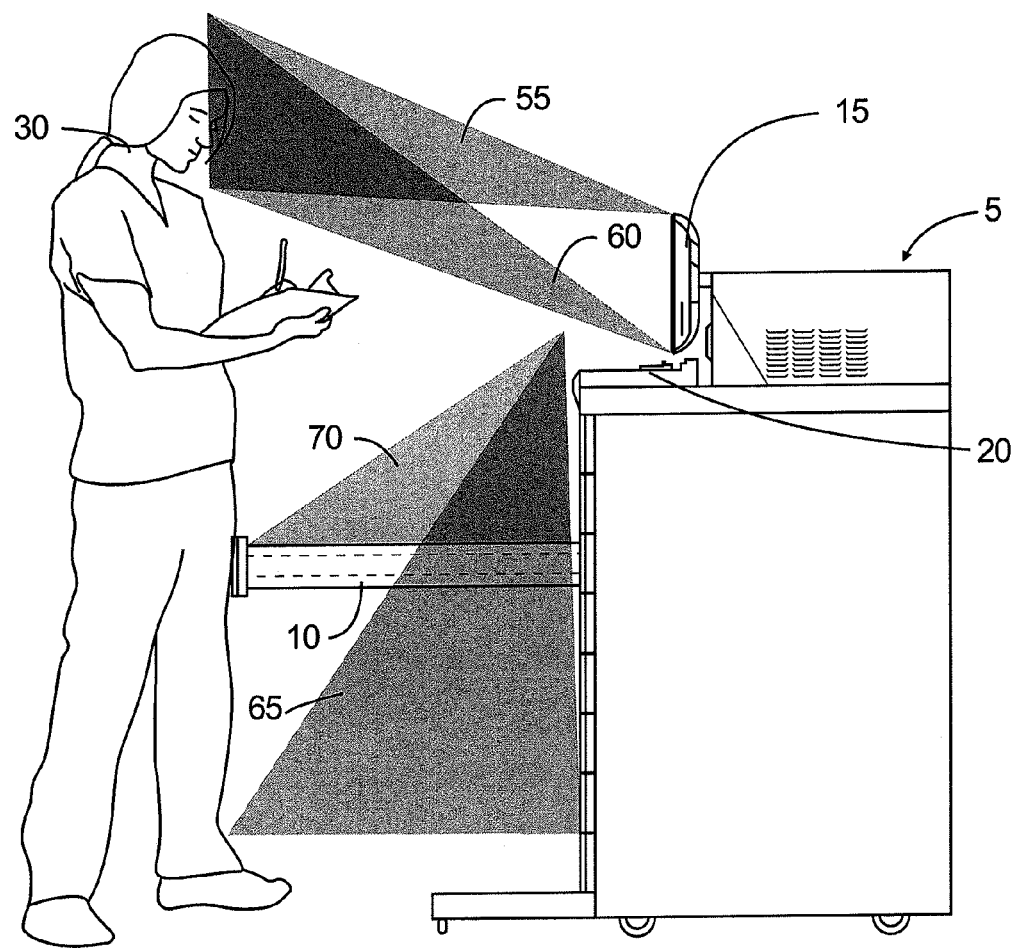

FIG. 4 shows a side view of the storage device 5 with example fields of view of the image capturing devices discussed above. For example, the camera 35 may have field of view 55, the camera 40 may have field of view 60, the camera 45 may have field of view 65, and the camera 50 may have field of view 70. Fields of view 55, 60, 65 and 70 may be utilized to observe various aspects of the storage device 5 and/or user 30. Unlike cameras located remote from the storage device 5 (e.g., in the ceiling of the room where the storage device 5 is located), it may be harder for the user 30 to hide actions from the image capturing devices included in the storage device 5 and the image capturing devices can be triggered based on specific actions by the storage device 5 (e.g., the unlocking of a drawer) and/or user interactions with the storage device 5 (e.g., the opening of an unlocked drawer). By triggering image capturing in response to one or more predefined trigger events, a more efficient surveillance, witnessing and/or other type of monitoring functionality can be realized than that used previously. For example, embodiments discussed herein may abrogate the need for data mining hours of video and/or scores of still images while conducting an investigation of suspected narcotic diversion. Additionally or alternatively, the image capturing by the image capturing devices included in the storage device 5 may be triggered individually, in groups and/or collectively (e.g., each image capturing device can be activated by itself and/or in response to a trigger event that causes at least one other image capturing device to be activated).

One or more of the fields of view 55, 60, 65 and 70 may be fixed and/or moveable in response to commands received by the associated image capturing device. For example, a processor and/or other control circuitry of the storage device 5 (some examples of which are discussed in connection with FIG. 7) may generate and transmit a command to camera 35, which causes camera 35 to direct downwards thereby causing field of view 55 to be directed relatively downwards to observe and/or verify the facial features of a relatively shorter user 30. Similarly, commands may be sent to any of the image capturing devices to otherwise control the functionality of the image capturing devices, including panning upwards, panning right, panning left, zooming in, zooming out, activating a different/additional mode (e.g., infra-red mode, backscatter mode, still picture mode, video mode, etc.), controlling a flash (or other light emitting device), and/or controlling any other functionality that may assist in capturing one or more images during a period of time. In this regards, one or more of the image capturing devices may be used for multiple purposes (e.g., first facial recognition and then scanning a machine-readable code on an identification tag worn or otherwise presented by the user 30). The commands generated and sent by the processor of the storage device 5 may be a result of pre-configured automatic functionality (e.g., panning down in response to determining the user 30 is relatively short) and/or a result of receiving a manual input (e.g., at the storage device and/or from a remote machine via a network, such as that discussed below in reference to FIG. 8). In this regard, each of the vantage points associated with the fields of view may be individually or collectively utilized, in response to determining that an activity of interest (such as accessing or stocking compartments that store narcotics) is occurring or may be about to occur within the field of view of the respective image capturing device(s).

Figure 5:
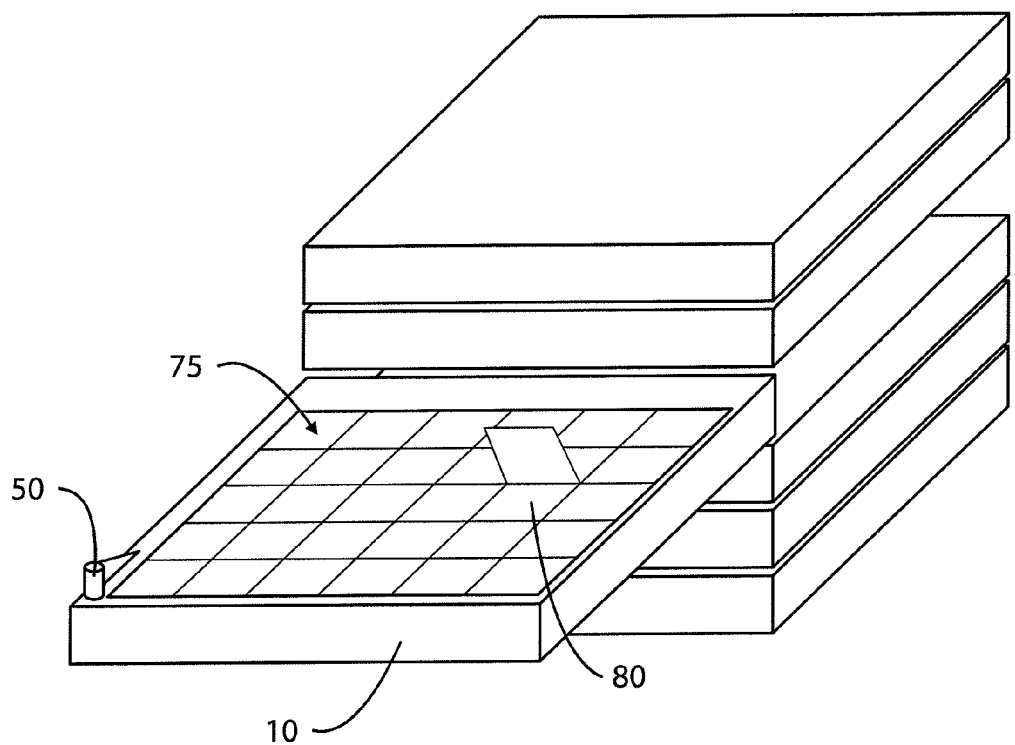
Figure 6:
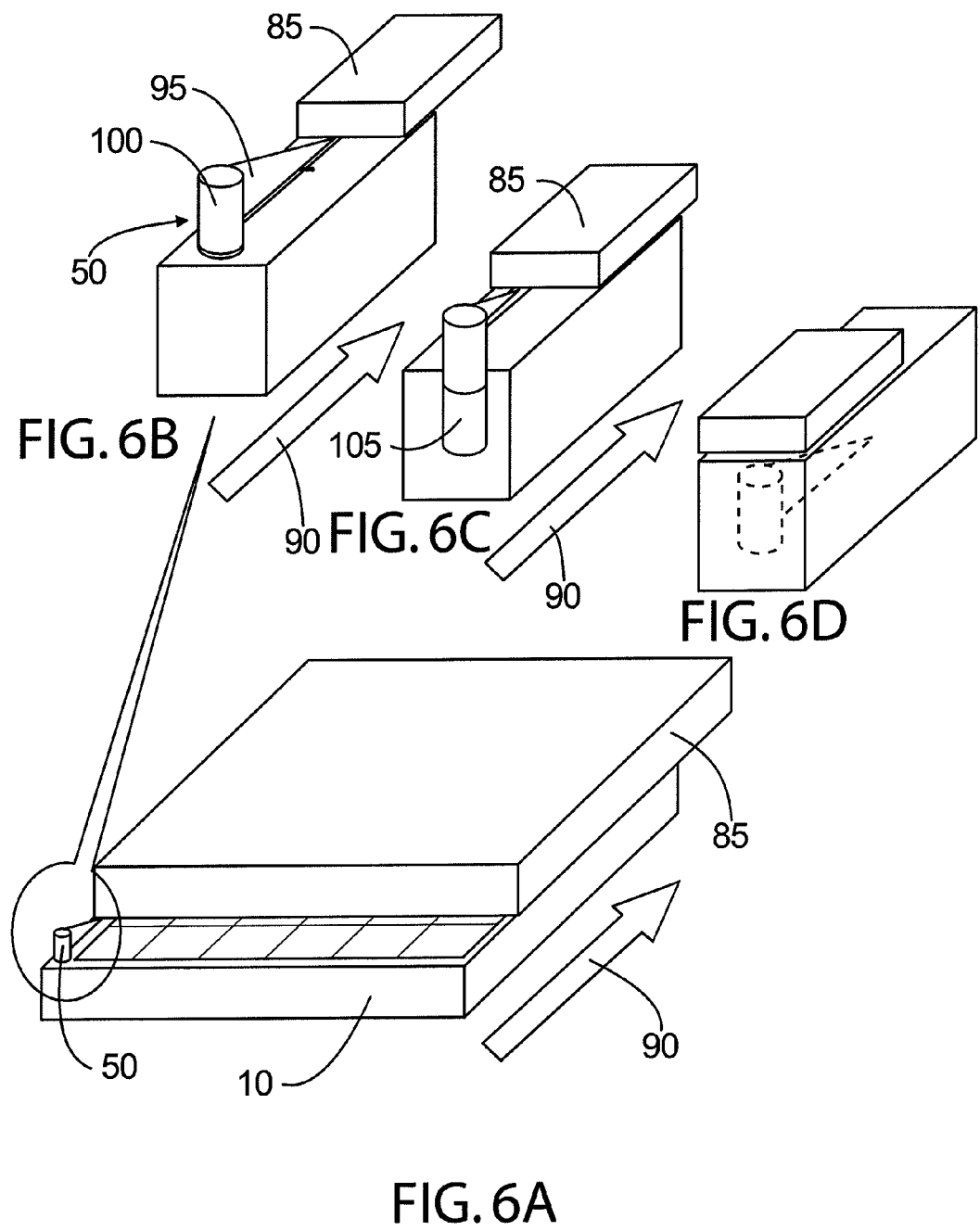

FIG. 5 shows a plurality of drawers, including the drawer 10, which may be included in the storage device 5. To avoid unnecessarily over complicating the drawing and discussion, a number of the other components of the storage device 5 have been omitted from FIG. 5. As noted above, the drawer 10 may include the drawer monitoring device 50, which can be configured to capture video and/or still images of the user's interactions with medication within the storage compartments 75. For example, when medication is placed into or removed from the medication compartment 80 (shown in FIG. 5 as being in the opened state), the drawer monitoring device 50 can be configured to have a field of view that includes the medication compartment 80 and be configured to capture one or more images of the interactions with medication compartment 80. As noted above, one or more external image capturing devices may simultaneously capture images identifying the user interacting with the medication compartment 80. In some embodiments, the drawer monitoring device 50 may be activated, for example, in response to: the drawer 10 being at least partially opened (e.g., extended outward from the other drawers as shown in FIG. 5), the medication compartment 80 being at least partially opened (e.g., the lid being in a position that allows access to the compartment, such as that shown in FIG. 5), the drawer 10 being unlocked or otherwise accessible by the control circuitry of the storage device 5, the medication compartment 80 being unlocked or otherwise accessible by the control circuitry of the storage device 5, the drawer monitoring device 50 detecting the presence of ambient light, the drawer monitoring device 50 being driven into a viewing position (that provides a vantage point of one or more medication storage compartments), and/or any other suitable trigger event.

Similarly, image capturing by the drawer monitoring device 50 (and/or any other imaging device included in the storage device 5) can be ceased in response to any suitable trigger event. For example, the image capturing may be ceased in response to determining: the drawer and/or compartment has been shut and/or locked, the user has logged-out of the system, the system has automatically logged the user out, the user has disabled the recording functionality, a remote user has disabled the recording functionality using a remotely located machine, and/or any other suitable trigger event. In some embodiments, the imaging devices of the storage device 5 may cease recording independently, in groups or collectively all together. For example, one or more of the imaging devices of the storage device 5 may have the same cease image capturing trigger event. In some embodiments, an alarm may be sounded locally at the storage device 5 and/or at a remote machine in response to determining one or more of the image capturing devices have stopped capturing images absent a trigger event to do so. For example, in response to determining that an image capturing device has been tampered with while recording, an alarm may sound from a speaker included in the storage device 5 and/or be displayed on a screen of a remote machine.

FIGS. 6A-6D show an example design and configuration of the drawer 10 having the drawer monitoring device 50, and how the drawer monitoring device 50 can be stowed into the drawer 10 as the drawer 10 is pushed closed and locked into the storage device 5. For example, FIGS. 6A and 6B show the drawer monitoring device being in the viewing position. While in the viewing position, the drawer monitoring device 50 can have a field of view that includes one or more compartments in the drawer 10 used to store medication(s). In FIG. 6C, the drawer monitoring device 50 is in a transitional position between the viewing position and the stowed position shown in FIG. 6D.

For example, the drawer monitoring device 50 may be any suitable imaging device, such as a spring loaded hi-definition fiber optic video camera with still camera capabilities. The drawer monitoring device 50 can include contact portion 95 and camera portion 100. As the drawer 10 is pushed and/or pulled closed relative the storage device 5 or otherwise moves in the direction of motion arrow 90, a portion of the adjacent drawer and/or other portion of the storage device 5 that is adjacent to the imaging device side of drawer 10, namely portion 85 in FIGS. 6A-6D, can be configured to physically contact the contact portion 95 and exert a force thereon. The contact portion 95 can include a beveled edge that is configured to drive the drawer monitoring device 50 into recess 105 included in the drawer 10 and shown in FIG. 6C, in response to the force exerted by portion 85 when the drawer 10 is moving in the direction of motion arrow 90. As shown in FIG. 6D, the drawer monitoring device may then reside inside the drawer 10 in a stowed position, while the drawer 10 is in the closed and/or locked position within the storage device 5.

When the drawer 10 is opened (e.g., moved in a direction opposite to that of motion arrow 90), the drawer monitoring device 50 may include an internal spring and/or other type of bias mechanism that enables the drawer monitoring device 50 to drive itself out of the recess 105 and into the viewing position show in, e.g., FIGS. 5 and 6A. Additionally or alternatively, a locking mechanism(s) may be included in the drawer 10 and/or the drawer monitoring device 50, which may cause the drawer monitoring device 50 to remain in the stowed position, even when the drawer 10 is open. In such embodiments, the locking mechanism(s) may need to be released before the potential energy stored in the compressed spring or other bias mechanism can drive the drawer monitoring device 50 into the viewing position shown in FIGS. 5, 6A and 6B. These are but examples and in some embodiments one or more other components and/or methods may additionally or alternatively be used to enable the monitoring of the drawer 10 and/or any other internal component of the storage device 5.

Figure 7:
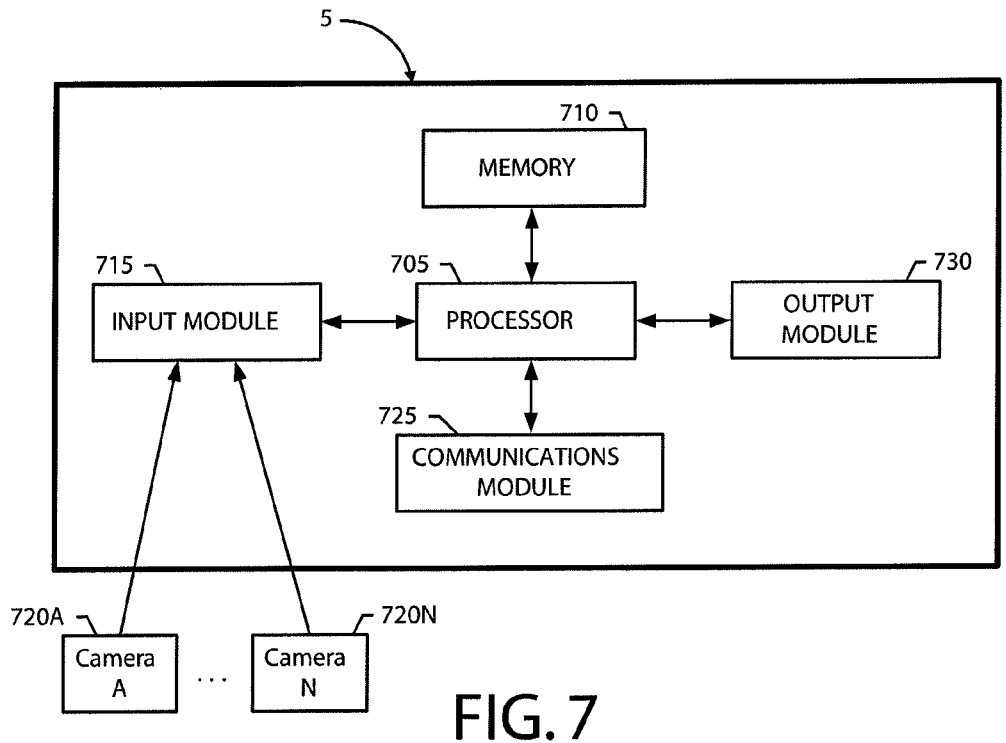
FIG. 7 is a block diagram of an apparatus that may be included in embodiments discussed herein.

Referring now to FIG. 7, the storage device 5 may include any type of circuitry to facilitate the functionality discussed herein. For example, circuitry commonly found in various computing devices and other types of machines (e.g., desktop computer, laptop computer, tablet, etc.), may be included in the storage device 5. For example, FIG. 7 shows a block diagram of example circuitry components that may be configured to store and/or execute computer-readable program code portions comprising executable instructions and/or other types of executable portions. As such, the storage device 5 may include various means for performing one or more functions in accordance with some embodiments, including those more particularly shown and described herein. It should be understood, however, that the storage device 5 may include alternative means for performing one or more like functions, without departing from the spirit and scope of embodiments discussed herein. As shown, the storage device 5 is a machine and can generally include means, such as processor 705 for performing or controlling the various functions of the storage device 5.

The processor 705 may, for example, be embodied as various means including one or more microprocessors with accompanying digital signal processor(s), processor(s) without an accompanying digital signal processor, one or more coprocessors, multi-core processors, controllers, computers, various other processing elements including integrated circuits such as, for example, an ASIC (application specific integrated circuit) or FPGA (field programmable gate array), or some combination thereof. Accordingly, although shown in FIG. 5 as a single processor, in some embodiments the processor 705 comprises a plurality of processors and/or any other type of control circuitry. The plurality of processors, for example, may be embodied on a single computing device or may be distributed across a plurality of computing devices collectively configured to function as the processor 705. The plurality of processors may be in operative communication with each other and may be collectively configured to perform one or more functionalities of the processor 705 as described herein. In an example embodiment, the processor 705 is configured to execute instructions stored in the memory 710 and/or that are otherwise accessible to the processor 705.

The memory 710 can be in communication with and/or included in the processor 705. The memory 710 may comprise volatile and/or non-volatile memory that stores content, data and/or any other information. For example, the memory 710 can store information generated by, transmitted from, and/or received by, the storage device 5. Also for example, the memory 710 typically stores software applications, instructions or the like for the processor 705 to perform steps associated with operation of the storage device 5. For example, the memory 710 may be a non-transitory storage medium that stores computer program code comprising instructions or other executable portions that the processor 705 executes to perform the steps described above and below with regard to, e.g., FIGS. 9-10.

These instructions, when executed by the processor 705, may cause the storage device 5 to perform one or more of the functionalities described herein. As such, whether configured by hardware, firmware/software methods, or by a combination thereof, the processor 705 may comprise an entity capable of performing operations according to embodiments of the present invention while configured accordingly. Thus, for example, when the processor 705 is embodied as an ASIC, FPGA or the like, the processor 705 may comprise specifically configured hardware for conducting one or more operations described herein. Alternatively, as another example, when the processor 705 is embodied as an executor of instructions, such as may be stored in the memory 710, the instructions may specifically configure the processor 705 to perform one or more algorithms and operations described herein.

For example, the memory 710 may include instructions for video processing and playback that allows hospital administrators and/or other users to actually see what happened during a transaction. In the past, if a nurse stole another user's access information and diverted medications while signed in as the other user, the nurse whose account was stolen may be mistakenly accused of diversion. Using the image(s) captured by embodiments discussed herein, investigators may be able to more easily identify with certainty who actually diverted the medications. As another example, the memory 710 may store instructions that enable screen capture functionality to record the onscreen events that are presented by the display device 15.

Figure 11:
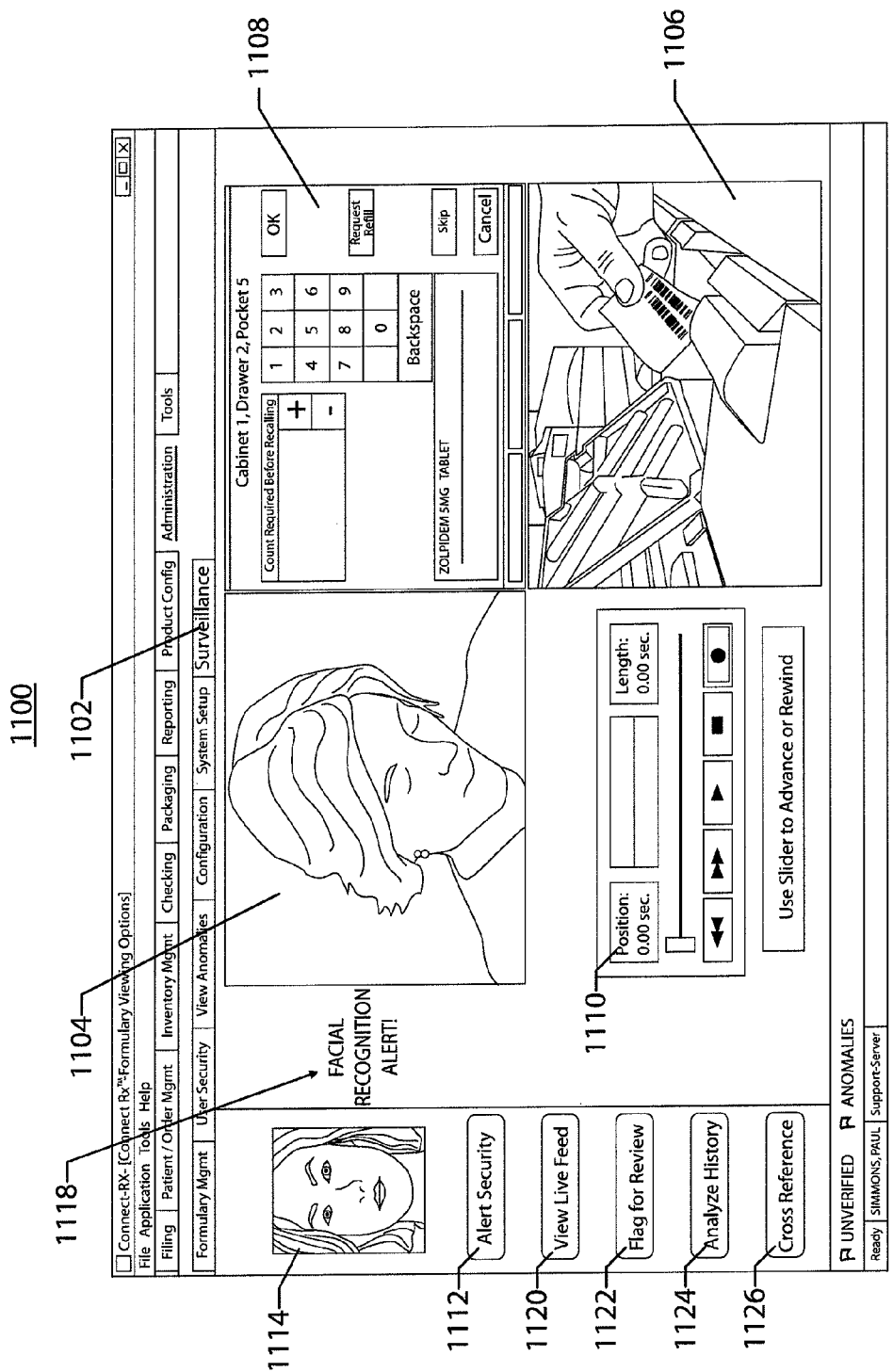
FIG. 11 is an example graphical user interface screen display that may be generated and presented by some embodiments of the present invention discussed herein.

As discussed below (in connection with, e.g., FIG. 8), the storage device 5 may be connected to a network and be configured to interface with one or more remote machines, such as data servers, databases, administrator machines, tablets, cellular devices, other mobile devices, etc. To facilitate this functionality, the memory 710 may also include instructions that are executable by the processor 705. For example, the memory 710 can store instructions that enable providing a central location surveillance data (e.g., image data, time stamps, etc.) captured by and/or related to that captured by the image capturing devices. As another example, the memory 710 can store instructions that enable generating and sending an alert to hospital security via email or other electronic means, such as in an instance in which an image of a user captured by a camera does not match a file image associated with the credentials of the user logged into the system. The memory 710 can also store or instead be configured to store instructions that enable providing an option for a live on-demand video feed(s) from the storage device 5. The memory 710 may also enable local and/or facilitate remote execution of instructions, for example, for facial recognition functionality, flagging of events for easy retrieval and review at a later time, instant reporting on the medication interaction activity history, allowing administrators and/or other users to cross reference the currently reviewed activity with other parameters (such as, e.g., user, medication, unit in a facility, medication pocket, etc.), and/or allowing for a unique, paneled approach to surveillance at the cabinet including, in particular, the key areas of the storage device in regards to a user's dispensing of medications. The paneled approach, an example of which is shown in FIG. 11, may include, among other things, a view of the current user, a view of the current pocket, drawer, bin, etc., a view of the current screen, and/or a scrubber that allows the administrator to view all events simultaneously as they actually occurred in time.

In addition to or instead of executing the instruction stored on the memory 710, the processor 705 may be configured to receive a signal from the input module 715, which may include specialized circuitry, one or more ports (serial, such as universal serial bus "USB" ports, and/or parallel ports), and/or any other component that facilitates the reception of signals from an input component. In some embodiments, the input module 715 can function as a user input interface and, in turn, receive data from any of a number and/or types of devices and/or users. For example, the input module 715 may be electrically coupled to the display device 15, the user input device 20 and/or the user input device 25. Similarly, one or more image capturing devices may be coupled to input module 715. Cameras 720A-720N represent, for example, the external camera 35, the external camera 40, the internal camera 45, the drawer monitoring device 50, and/or any other cameras that may be configured to provide data to the processor 705 of the storage device 5. Although more than one input module 715 can be included in the storage device 5, only one is shown in FIG. 7 to avoid overcomplicating the drawing (like the other components discussed herein).

Figure 8:
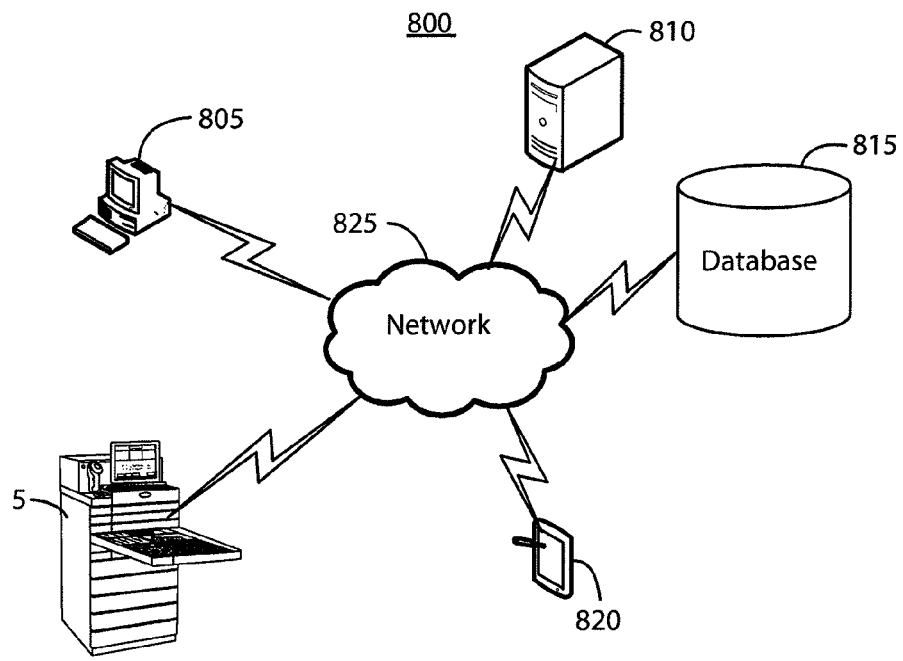
FIG. 8 is an example network in accordance with some embodiments discussed herein.

The processor 705 can also be configured to utilize the communications module 725 to communicate with one or more remote machines (e.g., via a network, such as that discussed in FIG. 8). The communications module 725 can include hardware, software, and/or any other means for transmitting and/or receiving data, content or any other type of information from a network or other type of device.

The processor 705 can be configured to communicate directly with one or more output components, such as display device 15, audio speaker(s), etc. In some embodiments, one or more output modules, such as output module 730 may enable processor 705 to interface with one or more output components. The output module 730 may include specialized circuitry, one or more ports (serial, such as universal serial bus "USB" ports, and/or parallel ports), and/or any other component that facilitates the output of signals to one or more output components included in the storage device 5. In this regard, the output module 730 can facilitate the functionality of one or more user interfaces and, in turn, provide information to a user using any number and/or types of devices. Although more than one output module 730 can be included in the storage device 5, only one is shown in FIG. 7 to avoid overcomplicating the drawing (like the other components discussed herein).

Referring to FIG. 8, system 800 is shown as an exemplary networked system that may benefit from embodiments provided herein. In addition to the storage device 5, system 800 may further include administrative machine 805, network 825, central server 810, database 815, and mobile device 820. The system 800 can be associated with a healthcare department, healthcare facility and/or entire enterprise in which the storage device 5 and/or other types of medication storage devices are being used or available for use. The storage device 5 may use the communications module 725 to access the network 825 and the other devices attached thereto, including the central server 810, in order to provide and/or receive image data signals as well as other types of signals (such as, e.g., metadata associated with the image data, commands to control the image capturing devices, etc.). The network 825 may include any wired or wireless communication network including, for example, a wired or wireless local area network (LAN), wide area network (WAN), or the like, as well as any hardware, software and/or firmware required to implement it (such as, e.g., network routers, etc.).

In response to receiving image and/or other related data (sometimes referred to herein as "monitoring data") from the storage device 5, the central server 810 may process and/or provide the monitoring data to the administrative machine 805, database 815, the mobile device 820, and/or any other networked devices (not shown) that may be used to view and/or otherwise interact with the monitoring data. For example, database 815 may store monitoring data (and/or other data) associated with one or more medication storage devices including, for example, image data, image metadata (e.g., time of day image was captured, user identified by facial recognition functionality, drawer, related images, etc.), storage device name, storage device location, types of medication being stored, remaining quantities of medication being stored, whether the device is in-use or available, user identifying information associated with the current user and/or previous user(s) of the device, error information (including, e.g., the type of error and the time the device went into the error state), and/or any other information that may aid in facilitating a subsequent investigation or other type of review of past events. In an alternative embodiment, some or all of the additional information associated with each of the medication storage devices may be stored in memory associated with each of the medication storage devices (e.g., the storage device 5), which central server 810 and/or the other medication storage devices can be configured to access, thus eliminating the need for database 815.

The administrative machine 805 can be any type of computing device, such as a personal computer, that can be configured to receive, process and/or present to a user some or all of the monitoring data generated by the storage device 5, including monitoring data that is being streamed in real time (including near-real time as understood by those skilled in the art) from the storage device 5 and/or previously stored at the database 815. In this regard, the administrative machine 805 can be used in place of a human witness that may otherwise sometimes be required when distributing narcotics from the storage device 5. For example, such embodiments may allow hospitals and/or other orginizations that need or desire an objective witness for narcotic transactions to be able to do so without needing a second human being at the storage device 5. This will save time and money because a human resource can then be used for more productive work.

Additionally or alternatively, the administrative machine 805 may be configured to assist in internal and external investigations regarding narcotic diversion. For example, the administrative machine 805 can be configured to enable administrators to access integrated video surveillance conducted by one or more storage devices, where the video surveillance is synchronized with events at the respective storage devices. The administrative machine 805 can also enable administrators to easily navigate to the video capture in question based on the metadata associated with the video data. The cameras at one or more of the storage devices may be concealed or disguised as to avoid direct notice by the user and/or prominently integrated into the storage device(s) so as to cause the user to notice the camera(s) and be deterred from any wrongdoing. The administrative machine 805 may also be configured to perform facial recognition functionality, flag specific users, among other things.

The mobile device 820 and/or any other type of device can also be configured to function the same as and/or provide similar or a subset of the functionality discussed in connection with the administrative machine 805. The mobile device 820 may be a tablet device, personal digital assistant, cellular phone, any other type of mobile device, or combination thereof that can be configured to enable a user to clearly identify someone who is interacting or previously interacted with a medication storage device, such as by viewing an image, video or the like, thereby eliminating substantial doubt about, for example, whether or not a nurse is logged in as herself and/or the physical activity of medications being placed in or pulled out of a secure pocket.

Additionally or alternatively, the components shown in FIG. 8 can be configured to, for example, provide an optional ability to send an alert to hospital security via email or other electronic means. For example, upon detecting a suspicious activity (e.g., narcotic diversion, unauthorized access to the storage device based on, e.g., a failure to manually or automatically facially match a user to his/her picture on file, tampering with a camera included in the storage device, etc.), the storage device 5, the administrator machine 805, the central server 810, the mobile device 820 and/or any other machine can be configured to generate and/or send an email message and/or other type of alert to the mobile device and/or computer of a security official.

As yet another example, the components shown in FIG. 8 can be configured to enable a user to flag one or more particular interactions with a storage device. For example, the system may automatically determine and/or allow a user to determine (e.g., at the administrative machine 805) that an interaction with a storage device may be of interest later. Metadata can then be generated in response to the user and/or system's determination and saved with the other monitoring data at, e.g., the database 815. The flag, similar to other metadata included in the surveillance data, may then be used to sort, search and/or filter image data for relatively quick review of particular interactions with the storage device.

One or more reports may also be generated based on the surveillance data. For example, reports may be generated based on data collected and stored by the system, wherein the reports are specific to, e.g., one or more storage devices, users of the storage device(s), drawers of the storage device(s), compartments of the storage device(s), times of day(s), locations, and/or any other suitable data. In this regard, the administrative machine 805 and/or the mobile device 820 can be configured to allow administrators and/or other users to cross reference and review a user's current activity at a storage device with previous activity by the same user, other user(s), same medication, other medication(s), same unit in the hospital, other unit(s), among other things. An example display that may be presented to enable such functionality is discussed in connection with, e.g., FIG. 11.

Figure 9:
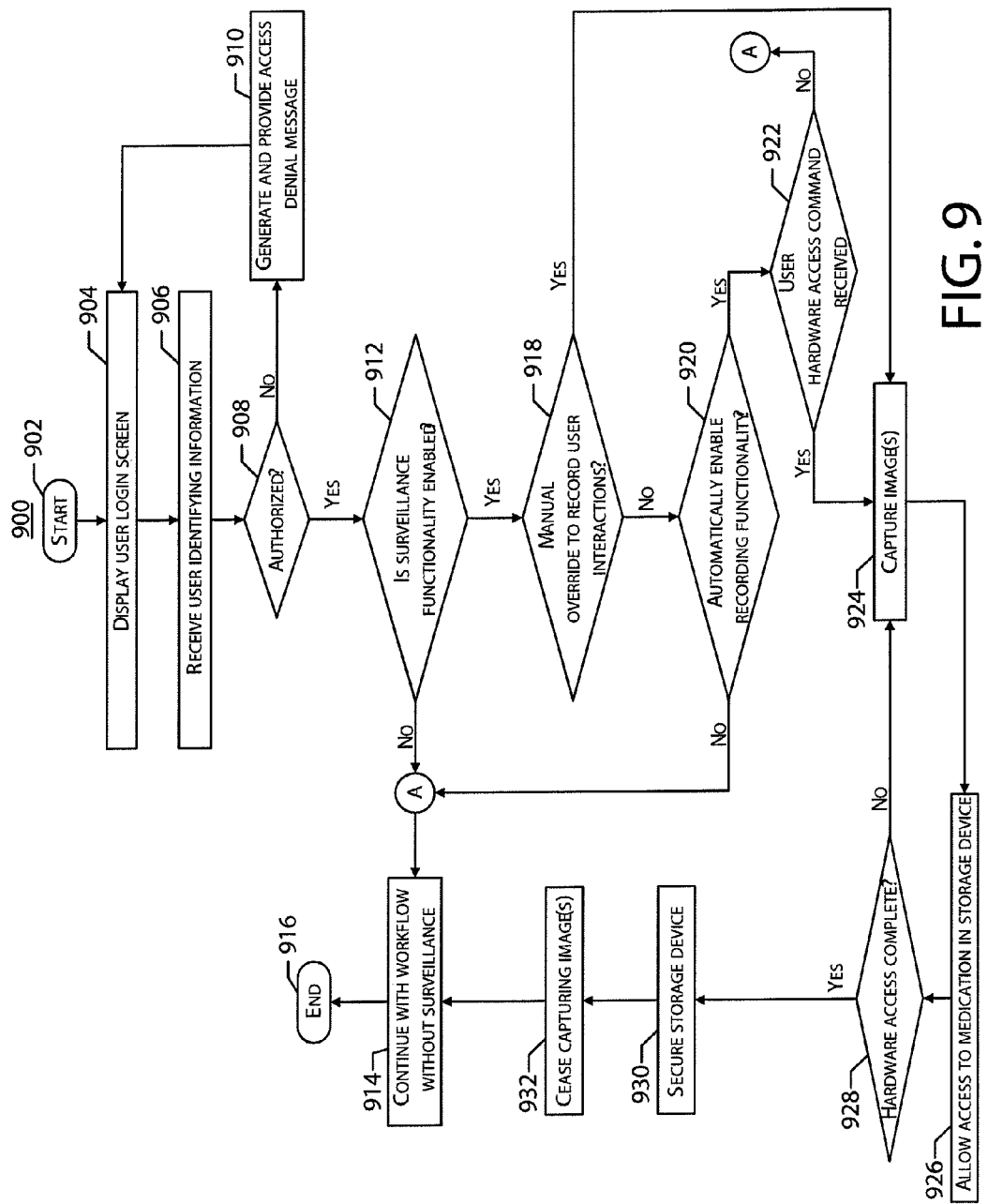
FIGS. 9 and 10 are flowcharts illustrating operations performed in accordance with some embodiments of the present invention.
Figure 10:
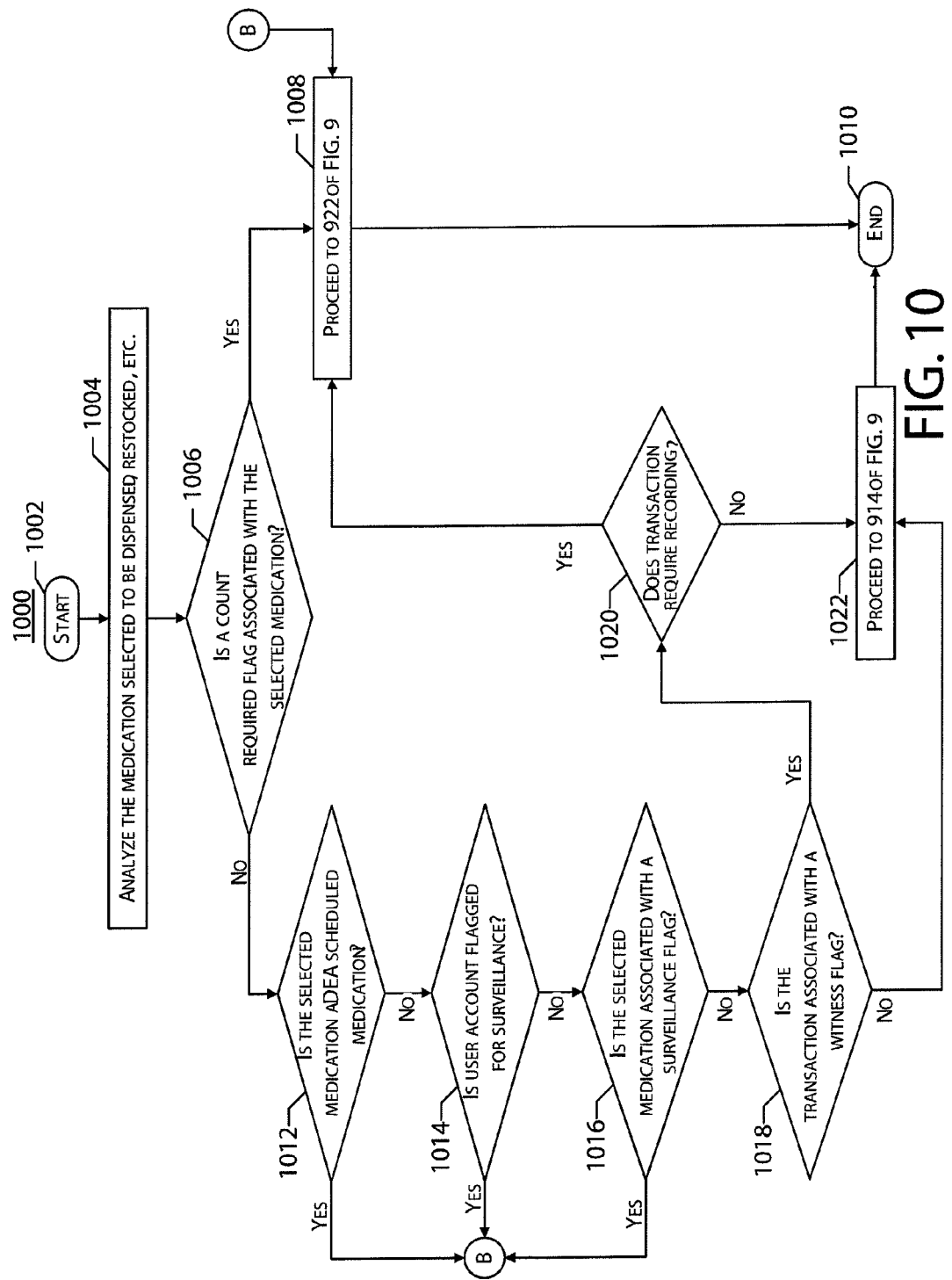

FIGS. 9 and 10 show processes 900 and 1000, respectively, which may be used in accordance with some embodiments to monitor the usage of a storage device, such as storage device 5 discussed herein. Processes 900 and 1000 are represented by flow diagrams in accordance with some exemplary methods, computer program products and/or systems discussed herein. It will be understood that each operation, action, step and/or other types of functions shown in the diagrams, and/or combinations of functions in the diagrams, can be implemented by various means. Means for implementing the functions of the flow diagrams, combinations of the actions in the diagrams, and/or other functionality of example embodiments of the present invention described herein, may include hardware and/or a computer program product including a computer-readable storage medium (as opposed to or in addition to a computer-readable transmission medium) having one or more computer program code instructions, program instructions, or executable computer-readable program code instructions stored therein. For example, program code instructions associated with FIGS. 9 and 10 may be stored on one or more storage devices, such as memory 710, and executed by one or more processors, such as processor 705. Additionally or alternatively, one or more of the program code instructions discussed herein may be stored and/or performed by distributed components, such as those that may be connected to storage device 5 via a network or other communications interface. As will be appreciated, any such program code instructions may be loaded onto computers, processors, other programmable apparatuses (e.g., storage device 5) or network thereof from one or more computer-readable storage mediums to produce a particular machine, such that the particular machine becomes a means for implementing the functions of the actions discussed in connection with, e.g., FIGS. 9, 10 and/or the other drawings discussed herein.

The program code instructions stored on the programmable apparatus may also be stored in a non-transitory computer-readable storage medium that can direct a computer, a processor (such as processor 705) and/or other programmable apparatus to function in a particular manner to thereby generate a particular article of manufacture. The article of manufacture becomes a means for implementing the functions of the actions discussed in connection with, e.g., FIGS. 9 and 10. The program code instructions may be retrieved from a computer-readable storage medium and loaded into a computer, processor, or other programmable apparatus to configure the computer, processor, or other programmable apparatus to execute actions to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel by one or more machines, such that multiple instructions are retrieved, loaded, and/or executed together. Execution of the program code instructions may produce a computer-implemented process such that the instructions executed by the computer, processor, other programmable apparatus, or network thereof provides actions for implementing the functions specified in the actions discussed in connection with, e.g., process 900 of FIG. 9.

Process 900 starts at 902 and proceeds to 904 where a user login screen is displayed. Like other displays discussed herein, a processor (such as the processor 705) and/or an output module (such as the output module 730) can generate a display and utilize a display device (such as the display device 15 and its circuitry) to present the display to the user (e.g., the user 30). The user login screen can prompt the user for various identifying information, including a user name, password, barcode, radio frequency identification ("RFID") access card, among other things. The storage device may obtain this information from, e.g., the various input components coupled thereto. Additionally, although many examples discussed herein refer to the storage device's and/or its processor's configuration, one or more other system components, such as a remotely located network device (e.g., the central server 810) and/or remote storage device (e.g., the database 815), may be configured to, used to provide and/or otherwise enable some of the functionality discussed herein.

At 906, the processor receives data associated with user identifying information from one or more user input components (e.g., via the input module 715, one or more image capturing devices, such as the external cameras discussed above, among other things).

At 908, a determination is made by the processor as to whether or not the user has provided valid authorization credentials. For example, images of the user's face can be automatically (using, e.g., facial recognition software) or manually compared with a valid picture of the user stored in memory, which is retrieved based upon other credentials the user provides (e.g., user name and password, barcode on an identification badge, etc.). In response to determining the user's credentials are not valid, process 900 proceeds to 910 and provides the user a notification that access will not be granted. The login screen may then be displayed again at 904 and the user or a new user may attempt to login again. In some embodiments, process 900 may end after a number of failed attempts and the processor may be configured to lock the storage device until an administrator or other predetermined user or type of user unlocks the storage device.

In response to determining at 908 that the user is authorized to access the storage device, process 900 proceeds to 912 and determines if surveillance functionality is enabled at the storage device that the user logged into at 908. For example, surveillance functionality may be considered not to be enabled in instances in which a storage device does not include image capturing devices, the image capturing devices are malfunctioning, and/or the storage device is otherwise not configured to conduct surveillance of one or more types of user interactions.

In response to determining at 912 that surveillance functionality is not enabled or is otherwise disabled, process 900 proceeds to 914 and the user's workflow involving the storage device is conducted without any surveillance. In some embodiments, data may be generated and saved at a central database and/or at the storage device, wherein the data is associated with transaction(s) conducted (e.g., dispensing of medication, restocking of medication, user identification information, time conducted, etc.), even when surveillance is not possible. After 914, process 900 can end at 916.

In response to determining at 912 that surveillance functionality is enabled, process 900 proceeds to 918 and a determination is made as to whether there is a manual override to record user interactions. In particular, while some embodiments may be configured to improve, among other things, efficiency of subsequent investigations by providing artificial intelligence as to when surveillance should be conducted (as opposed to always or periodically recording everything, regardless of what is occurring at the storage device), this intelligence can be by-passed in some embodiments by determining at 918 that a user has indicated a desire to manually override the algorithms that automatically monitor for image capturing trigger events. In other words, these features, like other features discussed herein, are optional and may or may not be included in some embodiments.

The determination at 912, like the other functions discussed herein, may be made by a processor (e.g., processor 710) included in the storage device (e.g., storage device 5), by a processor included in a network server (e.g., central server 810), a processor included in a networked machine (e.g., administrative machine 805), and/or any other suitable device.

In response to determining at 918 that a manual override to monitor user interactions was not received (e.g., at the storage device 5 and/or remote machine, such as administrative machine 805 or mobile device 820), computer program instructions embodying one or more algorithms can be executed to first determine, at 920, whether the user's interaction with the storage device 5 is of a type for which surveillance is desirable or required (i.e., whether the need or desire to capture an image of the user been triggered). FIG. 10 provides one example of how this determination could be made in accordance with one embodiment described herein. In response to determining at 920 that image capturing is not to be conducted (i.e., the interaction is not of a type for which surveillance is desirable or required) process 900 proceeds to 914 where the user continues with his or her workflow without surveillance.

Alternatively, in response to determining that image capturing is to be conducted by the storage device, process 900 proceeds to 922 and a determination is made as to whether or not a user hardware access command has been received (i.e., whether the actual image capturing has been triggered). For example, image capturing may not begin until the user and/or storage device causes the execution of a command that enables access to one or more of the cabinet drawers, remote refrigerators, and/or any other locations that may be within the field of view of an imaging device (e.g., as discussed above, in response to detecting (1) that the drawer and/or medication compartment is at least partially opened, (2) that the drawer and/or medication compartment is unlocked, (3) ambient light, (4) that the drawer monitoring device has been driven into a viewing position, and/or the like). In this regard, a relatively large percentage of images captured show users' interactions with the storage device that may be of interest to someone watching a live monitoring stream and/or later be of interest during an investigation.

In response to determining at 922 that a user hardware access command is never received, process 900 proceeds to 914. For example, if the user begins a workflow for dispensing narcotics using the storage device, but then walks away from the storage device and/or logs out of the storage device before opening a drawer or doing something that causes a compartment containing narcotics to unlock, the system can be configured to not capture and/or store (e.g., record) any of the user's interactions with the storage device (other than, e.g., the capturing of images for authorization purposes discussed above in connection with 906).

In response to determining at 922 that a user hardware access command is received, process 900 proceeds to 924 and a command to capture images is generated and/or provided to the storage device's image capturing device(s). For example, if one or more drawers in the storage device are opened, the drawer-specific image capturing devices and/or other internal cameras may begin recording video and/or taking and storing still pictures of the internal area of the storage device with which the user is interacting. In some embodiments, one or more external image capturing devices may also (or instead) be activated to, e.g., capture images(s) of the user that is interacting with the storage device. As such, some embodiments enable one or more particular image capturing devices of a plurality of image capturing devices to be activated simultaneously and synchronized. In some embodiments, the functionality at 922 (and/or any other step discussed herein), for example, may be omitted and the image capturing may begin in response to determining either a manual override has been detected at 918 and/or the system has determined at 920 that the transaction is of a type for which surveillance is desirable or required.

At 926, the system can allow the user to access the medication and/or other materials stored in the storage device. At 928, the system can monitor whether or not the user has finished accessing the storage device's hardware, and continue capturing images the entire time (e.g., continuously and/or periodically, such as ever second, couple of seconds, minute, etc.) that the user is accessing the storage device.

In response to determining at 928 that the user's hardware access is complete (e.g., the user has shut all drawers, has indicated through the visual interface that all interactions are done, has dispensed/stocked all medications on a predetermined list, etc.), the system can confirm the storage device is secured (e.g., locked) at 930.

At 932, image capturing can cease, so as to help prevent recording irrelevant content (e.g., anything that does not involve a user's interactions with medications and/or other supplies included in the storage device). After 932, process 900 can return to 914 discussed above.

FIG. 10 shows process 1000, which is an example of a process including various algorithms that may be executed at 920 of FIG. 9. As discussed above, the determinations made in process 1000 can each be associated with one or more surveillance trigger events that cause the image capturing devices to automatically begin recording and/or otherwise capturing content either immediately or after a user hardware access command is received (e.g., in response to detecting the drawer and/or medication compartment being opened and/or unlocked, etc.).

Process 1000 begins at 1002 and proceeds to 1004. At 1004, the system can be configured to analyze the medications that have been selected for dispensing, restocking, etc.

For example, the system can be configured to analyze at 1004 information received from or at the storage device based on the user's interactions with one or more interactive displays presented by the storage device. That is, after logging into the storage device and the system discussed in reference to FIG. 8, the system and/or storage device may generate a list of medications to be dispensed, counted and/or stocked by the user based on the user's job responsibilities, patient needs, time of day, etc. The analysis at 1004 can include, for example, a search for metadata and/or other information that may be used by the algorithms that monitor for a surveillance trigger event.

For example, the analysis at 1004 can include searching for a count required flag among the metadata that is associated with a medication selected from the list of the medications included in the generated list. A count required flag may be a 1 or 0 (or other type of code) that indicates whether or not a pharmacy has indicated that the particular medication needs to be counted by a user who (theoretically) does not know how many doses of medication should be in the compartment. This type of count is sometimes referred to as "a blind count."

In response to determining at 1006 that the count required flag is associated with a medication to be interacted with, process 1000 proceeds to 1008, at which process 900 may resume at 922 and/or any other step that may lead to capturing images of the user's interactions with the storage device and/or the particular medication either immediately or after receiving a user hardware access command.

In response to determining at 1006 that there is no count required flag associated with a medication to be interacted with, process 1000 proceeds to evaluate whether the user's interaction falls within a series of different types of interactions for which surveillance would be desirable or required. For example, at 1012, a determination is made as to whether a third party requires or suggests the monitoring of the selected medication. For example, the Drug Enforcement Agency ("DEA") has a schedule of parent chemicals that are included in some drugs that cause the drugs to be controlled. Some embodiments can be configured to capture images of the user and/or one or more components of the storage device in response to determining at 1012 that these types of drugs are being interacted with. As such, in response to making such a determination, process 1000 proceeds to 1008.

In response to determining that the selected medication is not a DEA scheduled medication, a determination can be made at 1014 whether or not the user account (and/or, more generally, the user) has been flagged for surveillance. A user may be identified based upon his/her account information (e.g., user name and password) and/or his/her image as captured by the external camera(s) included in the storage device.

The user may be flagged for surveillance automatically by the system and/or manually by an administrator (and/or any other user) if the user accessing the storage device is, for example, suspected of stealing medications and/or some other past/future wrong doing, is randomly selected for monitoring, is known to be acquainted with and/or related to someone who has been accused or caught doing something wrong, is a trainee who needs to be monitored for quality purposes, and/or for any other reason that may be unique to one user as compared to another. Another example advantage realized by this feature is that a pharmacy can track the cabinet activities of a particular user. In response to determining at 1014 that the user's account is flagged for surveillance, process 1000 can proceed to 1008.

In response to determining at 1014 that the user is not flagged for surveillance, process 1000 can proceed to 1016 and determine whether the medication is otherwise associated with a surveillance flag. For example, some medications that are not on the DEA's schedule of medications and do not require a blind count by a pharmacy, may still be flagged for surveillance by an administrator and/or other user. This feature may allow, for example, a pharmacist to flag a particular medication for surveillance due to the danger posed by the use/handling of the medication, the expense of the medication, or for any reason the pharmacist or other user determines it prudent to survey transactions involving this drug. In some embodiments, the system may automatically assign a surveillance flag to a medication. For example, the system may be configured to look for patterns (such as patterns of diversions) based on interactions with a plurality of storage devices, and proactively flag medications for monitoring, even if human users have yet to determine that a particular medication needs to be monitored. In other words, the system may have access to real time data that suggests it would be prudent to monitor a particular medication. Similarly, the system can flag a user for monitoring automatically. As yet another example, a medication may be randomly assigned for surveillance and have a surveillance flag associated therewith. In response to determining at 1016 that the medication is flagged for surveillance, process 1000 can proceed to 1008.

In response to determining at 1016 that the user is not flagged for surveillance, process 1000 can proceed to 1018 and determine whether the medication is associated with a witness flag. This feature can be used to provide a video record of a transaction when a human witness of the transaction may otherwise or additionally be required. A witness flag may be used when, e.g., a human witness is unavailable, the pharmacy and/or other department would like a video record of the transaction regardless of a witness being present, and/or for any other reason.

In response to determining at 1018 that a witness flag is associated with the medication, a determination can be made at 1020 whether or not the transaction requires recording. For example, if a human witness is available, the transaction may not need to be recorded despite there being a witness flag associated with the medication. However, in some embodiments, even if a human witness is available, some embodiments may still require electronic monitoring of the transaction by the image capturing devices, and step 1020 may be omitted from process 1000 as the witness flag may not be allowed to be overridden. In some embodiments, when surveillance is enabled on a witness-required medication, additional or alternative options (and decision blocks, which are not shown) could be used to determine whether or not the user is allowed to bypass a witness requirement in favor of video recording, or if the user must witness and the video would record then as well. In such cases, the algorithm(s) can include logic to respect these (and/or other) options. Additionally or alternatively, other functions discussed herein may be overridden despite such logical steps not being shown or discussed in the drawings.

In response to determining at 1020 that the transaction does not require recording (e.g., the witness flag can be overridden by a human witness at the storage device), process 1000 proceeds to 1022 and the functions of 914 of FIG. 9 are executed. Process 1000 then ends at 1010. In response to determining at 1020 that the transaction does require electronic surveillance (e.g., the witness flag cannot be overridden by a human witness at the storage device, there is no human witness at the storage device, the human witness is not verifiable and/or does not have the authority to override the witness required flag, etc.), process 1000 proceeds to 1008.

As noted above, the trigger events discussed above are examples only and are not meant to be limiting. Other trigger events for image capturing may additionally or alternatively be included in process 1000. For example, a manual-override trigger event may occur when a storage device is unlocked and entered into a manual mode in which all of its drawers, storage compartments, etc. are unlocked and made accessible to any user. Such manual overrides usually only occur during natural disasters and/or other events where the control of medication is second to the welfare of the public and patients.

As another example, there may also be a transaction-based trigger event that causes the automatic image capturing when a particular type of transaction is detected. Such a feature can allow, for example, a pharmacist to monitor activities at the storage device that are unusual for a given medication device, hospital unit, delivery site, system option, etc. For example, a transaction-based trigger event may occur when a drug usually given to the elderly is accessed in a prenatal unit. As another example, a transaction-based trigger event may include specific transaction types that administrators pick from a list of transaction types to record (such as override dispenses or recalls).

Furthermore, although process 1000 is shown as a single process to avoid unnecessarily overcomplicating the discussion, one or more of the algorithms discussed in connection with FIG. 10 may have its own process, may be combined with other algorithms (which may or may not be explicitly discussed herein), may be omitted from process 1000, and/or may be reordered within process 1000 (and/or any other process that is or is not explicitly discussed herein).

FIG. 11 shows an example display, namely display 1100, that may be presented on a display screen of, e.g., the administrative machine 805, the mobile device 820, and/or any other machine that may be included in systems that are in accordance with embodiments discussed herein. Display 1100 is shown as including a number of tabs and other selectable options. For example, when tab 1102 is selected, a paneled approach may be provided that enables surveillance of interactions that occurred and/or are occurring at a storage device.

Display 1100 also includes portion 1104, which may show a view of the user as captured by external image capturing device at the storage device. Portion 1106 of display 1100 may include a view of the current pocket, drawer, bin, etc. that is/was interacted with and observed by internal image capturing devices. Portion 1108 of display 1100 may show what is/was being displayed by the storage device's display screen. The images shown in portions 1104, 1106 and 1108 can be synchronized in time as they occur/occurred at the storage device.

Display 1100 may also include one or more interactive components that an administrator and/or other user can use to control and/or otherwise manipulate the storage device and/or data generated thereby. For example, scrubber 1110 can be provided in display 1100 and allow the administrator and/or other person viewing display 1100 to rewind and/or fast forward monitoring data, including image data, used to generate the images shown in portions 1104, 1106 and/or 1108, if desired.

As another example, an alert security button 1112 can be included and used to call security. In response to selecting the alert security button 1112, for example, a message can be sent to security that identifies a particular storage device and its location for investigation. The user may select the alert security button 1112 when, for example, the image known to be the user logged into the storage device and shown in portion 1114 does not match the image of the person actually using the storage device as shown in portion 1104. In some embodiments, the system may provide facial recognition functionality and automatically determine whether the known image in portion 1114 matches that being captured by the storage device and shown in portion 1104. When the facial recognition feature indicates that the known image of the user does not match that of the current user, an alert may be presented in portion 1118.

Another example of an interactive component, display 1100 can include a live feed button 1120. In response to selecting the view live feed button 1120, a live feed can be provided in portion 1104, portion 1106 and/or portion 1108.

As yet another example of an interactive component, display 1100 can include a flag for review button 1122. In response to selecting the flag for review button 1122, a flag (e.g., metadata) can be associated with the content (e.g., image(s) shown in portion 1104, portion 1106 and/or portion 1108). The flag can then be used to retrieve the content that the user thought was worth flagging more quickly than had the content not been flagged. The flag may also identify the administrator and/or other user that is logged into the system and selects the flag for review button 1122.

The analyze history button 1124 can also be generated and presented by some embodiments. The analyze history button 1124 can cause the system to conduct an analysis of a particular user and/or user's history at one or more storage devices on the system.

As another example of an interactive component, display 1100 can include a cross reference button 1126. In response to selecting the cross reference button 1126, a one or more additional displays may be presented that enable the administrator or other user of display 1100 to cross reference, for example, the currently reviewed activity with other parameters, such as parameters related to a user, medication, unit, storage compartment, and/or any other type of metadata associated with monitoring data. In some embodiments, the functionality associated with the various buttons discussed herein can be activated in any suitable manner, in addition to or instead of the buttons discussed herein.

In this regard, embodiments discussed herein can assist in, among other things, decreasing or eliminating the need for a witness, assisting in identifying a user of a storage device, verifying the medication storage compartment in question (e.g., that being interacted with), producing a recording of exactly how many medications were placed into or taken out of the storage device, increasing the certainty of exactly what took place during an event involving a narcotic at the cabinet, decreasing time to resolve discrepancies that do not have an obvious answer, increasing patient/medication safety, increasing audit capabilities at the cabinet remotely from the pharmacy, providing administrators and other remote users the option of seeing live camera feeds at any time, pre-identifying events by tagging and sending alerts to personal to conduct remote or in-person review for suspicious activity, providing links on reports to the video archive in question to enable administrators to conveniently review suspicious activity, and/or providing a more effective deterrent to narcotic diversion. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A storage device for dispensing medications, comprising:
    at least one drawer configured to store a plurality of medications; and
    at least one medication observation camera integrated into each drawer of the at least one drawer of the storage device, the medication observation camera configured to capture one or more medication images having an internal field of view of a user's interactions with at least one of the medications stored in the respective drawer, wherein the medication observation camera defines a viewing position and a stowed position, wherein the medication observation camera is biased toward the viewing position, wherein the medication observation camera moves from the stowed position to the viewing position in response to the drawer being moved to the open position, wherein the medication observation camera is driven against the bias toward the stowed position in response to the drawer being moved to the closed position, wherein the medication observation camera comprises a contact portion having a beveled edge, and wherein a portion of the storage device is configured to advance along the beveled edge and drive the medication observation camera into the stowed position within the recess in response to the drawer being moved to the closed position;
    at least one user observation camera configured to capture one or more user images of the user; and
    at least one processor, wherein the processor is configured to:
        cause the medication observation camera to begin capturing the medication images in response to the processor determining that the drawer is open;
        receive medication image data representing the medication images captured by the observation camera and user image data captured by the user observation camera;
        cause the transmission of the medication image data to a remote machine; and
        cause the transmission of user image data to the remote machine, the user image data representing the user images, wherein the user image data and the medication image data both include metadata that enable the user image data and the medication image data to be synchronized in time.

2. The storage device of claim 1, wherein the medication observation camera is configured to begin capturing the medication images in response to the processor determining that a trigger event has occurred.

3. The storage device of claim 1, wherein the medication observation camera is configured to begin capturing the medication images in response to the processor determining that the drawer is accessible.

4. The storage device of claim 1 wherein the at least one user observation camera is configured to capture one or more user images having an external field of view of the user.

5. The storage device of claim 4, wherein the user observation camera is configured to capture the user images while the medication observation camera captures the medication images.

6. The storage device of claim 1, wherein the processor is configured to:
receive a command from a remote machine; and
in response to receiving the command, cause the transmission of a real time or near-real time video feed to the remote machine, the video feed including image data that represents the medication images.

7. The storage device of claim 1 further comprising a display device configured to present a graphical user interface display, wherein the processor is configured to:
generate display data that causes the presentation of the graphical user interface display; and
cause the transmission of the display data, wherein the display data includes metadata that enables the display data, the user image data and the medication image data to be synchronized in time.

8. A method for dispensing medications from a storage device, comprising:
storing a plurality of medications in at least one drawer;
capturing, using at least one medication observation camera integrated into each drawer of the at least one drawer of the storage device, one or more medication images of a user's interactions with at least one of the medications stored in the respective drawer, wherein the medication observation camera defines a viewing position and a stowed position, wherein the medication observation camera is biased toward the viewing position, wherein the medication observation camera moves from the stowed position to the viewing position in response to the drawer being moved to an open position, wherein the medication observation camera is driven against the bias toward the stowed position in response to the drawer being moved to a closed position, wherein the medication observation camera comprises a contact portion having a beveled edge, and wherein a portion of the storage device is configured to advance along the beveled edge and drive the medication observation camera into the stowed position within the recess in response to the drawer being moved to the closed position;
causing the medication observation camera to begin capturing the medication images in response to determining that the drawer is in the open position;
receiving medication image data representing the medication images captured by the observation camera;
transmitting the medication image data to a remote machine;
capturing, using at least one user observation camera, one or more user images of the user;
synchronizing the user image data and the medication image data to be displayed simultaneously by the remote device; and
transmitting user image data to the remote machine, the user image data representing the user images.

9. The method of claim 8 further comprising begin capturing the medication images in response to a determination by a processor that a trigger event has occurred.

10. The method of claim 8 wherein capturing the medication images begins in response to a determination by a processor that the drawer is accessible.

11. The method of claim 10 further comprising capturing the user images while the medication observation camera captures the medication images.

12. The method of claim 8 further comprising capturing, using at least one user observation camera, one or more user images of the user.

13. The method of claim 8 further comprising:
receiving a command from a remote machine; and
in response to receiving the command, causing the transmission of a real time or near-real time video feed to the remote machine, the video feed including image data that represents the medication images.

14. The method of claim 8 further comprising:
presenting, using a display device at the storage device, a graphical user interface display;
generating display data that represents the graphical user interface display;
synchronizing the display data, the user image data and the medication image data to be displayed simultaneously by the remote device; and
transmitting the display data to the remote machine.

15. A medication storage device, comprising:
a drawer defining an open position and a closed position, the drawer further defining a recess configured to receive an image capturing device, the drawer comprising:
an image capturing device defining a stowed position and an viewing position, wherein the image capturing device is biased toward the viewing position, and wherein the image capturing device is configured to be stowed in the recess; and
a compartment configured to store medication wherein the image capturing device moves from the stowed position to the viewing position in response to the drawer being moved to the open position, wherein the image capturing device is driven against the bias toward the stowed position in response to the drawer being moved to the closed position, wherein the image capturing device comprises a contact portion having a beveled edge, and wherein a portion of the storage device is configured to advance along the beveled edge and drive the image capturing device into the stowed position within the recess in response to the drawer being moved to the closed position;
wherein the image capture device is configured to advance via the bias to the viewing position in response to the drawer being moved to the open position, and wherein the image capture device is configured to be driven against the bias into the stowed position within the recess in response to the drawer being moved from the open position to the closed position.

16. The medication storage device of claim 15, wherein the image capturing device includes a spring that is configured to drive the image capturing device from the recess into a viewing position in response to the drawer being placed in an open position relative to the medication storage device.

17. The medication storage device of claim 16, wherein the viewing position enables the image capturing device's field of view to include one or more compartments in the drawer used to store medication.

18. The medication storage device of claim 16, where the image capturing device is configured to begin capturing images in response to being placed into the viewing position.

* * * * *